(12) United States Patent
Gao et al.

(10) Patent No.: US 10,540,591 B2
(45) Date of Patent: Jan. 21, 2020

(54) DEEP LEARNING-BASED TECHNIQUES FOR PRE-TRAINING DEEP CONVOLUTIONAL NEURAL NETWORKS

(71) Applicant: Illumina, Inc., San Diego, CA (US)

(72) Inventors: Hong Gao, Palo Alto, CA (US);
Kai-How Farh, San Mateo, CA (US);
Samskruthi Reddy Padigepati, Sunnyvale, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/407,149

(22) Filed: May 8, 2019

(65) Prior Publication Data

US 2019/0266493 A1 Aug. 29, 2019

Related U.S. Application Data

(63) Continuation-in-part of application No. 16/160,903, filed on Oct. 15, 2018, now Pat. No. 10,423,861, and (Continued)

(51) Int. Cl.
*G06K 9/62* (2006.01)
*G06N 3/12* (2006.01)
*G06N 3/08* (2006.01)

(52) U.S. Cl.
CPC .............. *G06N 3/123* (2013.01); *G06N 3/08* (2013.01)

(58) Field of Classification Search
USPC ................................................. 382/156–157
See application file for complete search history.

(56) References Cited

U.S. PATENT DOCUMENTS

2016/0357903 A1    12/2016  Shendure et al.
2018/0330824 A1*   11/2018  Athey .................... G16B 20/00

OTHER PUBLICATIONS

Zhang, Jun, and Bin Liu. "PSFM-DBT: identifying DNA-binding proteins by combing position specific frequency matrix and distance-bigram transformation." International journal of molecular sciences 18. 9 (2017): 1856. (Year: 2017).*

(Continued)

*Primary Examiner* — Sean M Conner
(74) *Attorney, Agent, or Firm* — Haynes Beffel & Wolfeld, LLP; Ernest J. Beffel, Jr.; Paul A. Durdik

(57) ABSTRACT

The technology disclosed includes systems and methods to reduce overfitting of neural network-implemented models that process sequences of amino acids and accompanying position frequency matrices. The system generates supplemental training example sequence pairs, labelled benign, that include a start location, through a target amino acid location, to an end location. A supplemental sequence pair supplements a pathogenic or benign missense training example sequence pair. It has identical amino acids in a reference and an alternate sequence of amino acids. The system includes logic to input with each supplemental sequence pair a supplemental training position frequency matrix (PFM) that is identical to the PFM of the benign or pathogenic missense at the matching start and end location. The system includes logic to attenuate the training influence of the training PFMs during training the neural network-implemented model by including supplemental training example PFMs in the training data.

24 Claims, 15 Drawing Sheets

Related U.S. Application Data a continuation-in-part of application No. 16/160,986, filed on Oct. 15, 2018, and a continuation-in-part of application No. PCT/US2018/055840, filed on Oct. 15, 2018, and a continuation-in-part of application No. PCT/US2018/055878, filed on Oct. 15, 2018, and a continuation-in-part of application No. PCT/US2018/055881, filed on Oct. 15, 2018.

(60) Provisional application No. 62/573,144, filed on Oct. 16, 2017, provisional application No. 62/573,149, filed on Oct. 16, 2017, provisional application No. 62/573,153, filed on Oct. 16, 2017, provisional application No. 62/582,898, filed on Nov. 7, 2017.

(56) References Cited

OTHER PUBLICATIONS

Gao, Tingting, et al. "Identifying translation initiation sites in prokaryotes using support vector machine." Journal of theoretical biology 262.4 (2010): 644-649. (Year: 2010).*

Bi, Yingtao, et al. "Tree-based position weight matrix approach to model transcription factor binding site profiles." PloS one6.9 (2011): e24210. (Year: 2011).*

Korhonen, Janne H., et al. "Fast motif matching revisited: high-order PWMs, SNPs and indels." Bioinformatics 33.4 (2016): 514-521. (Year: 2016).*

Wong, Sebastien C., et al. "Understanding data augmentation for classification: when to warp?." 2016 international conference on digital image computing: techniques and applications (DICTA). IEEE, 2016. (Year: 2016).*

Chang, Chia-Yun, et al. "Oversampling to overcome overfitting: exploring the relationship between data set composition, molecular descriptors, and predictive modeling methods." Journal of chemical information and modeling 53.4 (2013): 958-971. (Year: 2013).*

Li, Gangmin, and Bei Yao. "Classification of Genetic Mutations for Cancer Treatment with Machine Learning Approaches." International Journal of Design, Analysis and Tools for Integrated Circuits and Systems 7.1 (2018): 63-67. (Year: 2018).*

Martín-Navarro, Antonio, et al. "Machine learning classifier for identification of damaging missense mutations exclusive to human mitochondrial DNA-encoded polypeptides." BMC bioinformatics 18. 1 (2017): 158. (Year: 2017).*

Angermueller, et. al., "Deep Learning for Computational Biology", 2016, 16pgs.

Krizhevsky, Alex, et al, ImageNet Classification with Deep Convolutional Neural Networks, 2012, 9 Pages.

Geeks for Geeks, "Underfitting and Overfilling in Machine Learning", [retrieved on Aug. 26, 2019]. Retrieved from the Internet <https://www.geeksforgeeks.org/underfitting-and-overfitting-in-machine-learning/>, 2 pages.

Despois, Julien, "Memorizing is not learning!—6 tricks to prevent overfitting in machine learning", Mar. 20, 2018, 17 pages.

Bhande, Anup What is underfitting and overfitting in machine learning and how to deal with it, Mar. 11, 2018, 10pages.

PCT/US2019031621—International Search Report and Written Opinion dated Aug. 7, 2019, 17 pages.

Sundaram et al., "Predicting the clinical impact of human mutation with deep neural networks," Nature genetics 50, No. 8 (2018): pp. 1161-1173.

Carter et al., "Cancer-specific high-throughput annotation of somatic mutations: computational prediction of driver missense mutations," Cancer research 69, No. 16 (2009): pp. 6660-6667.

* cited by examiner

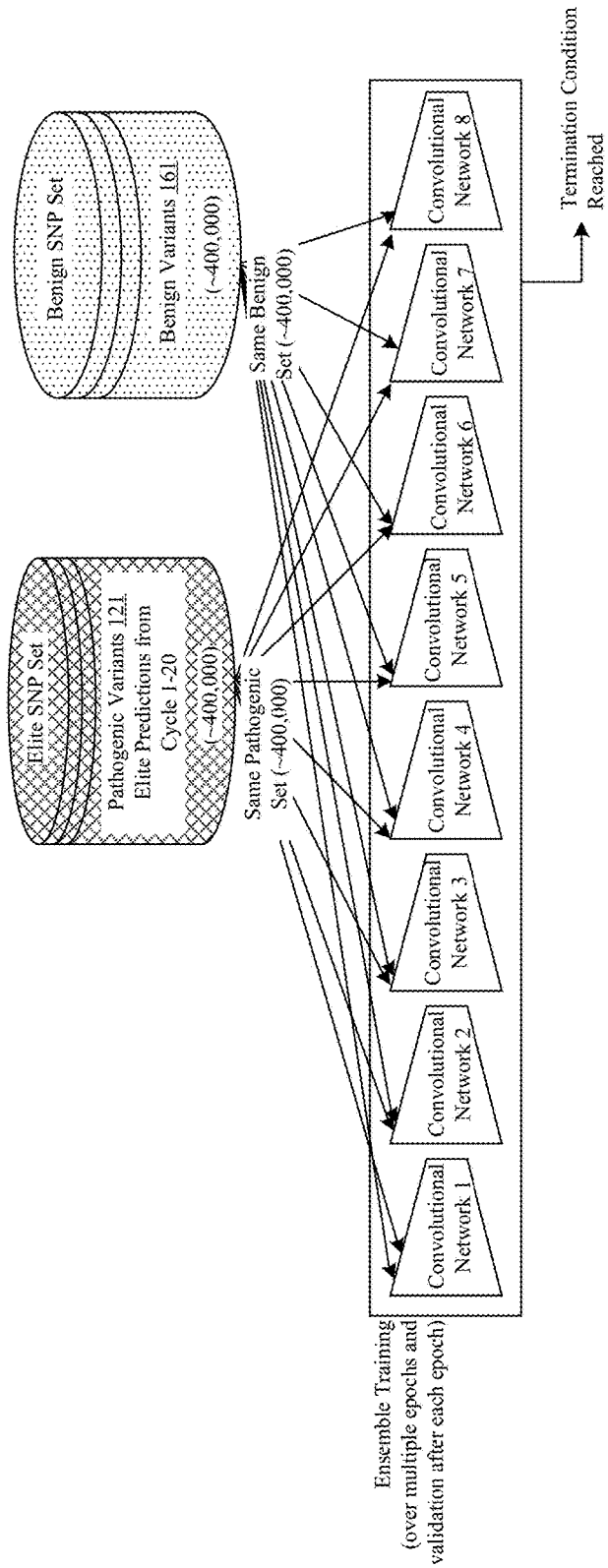
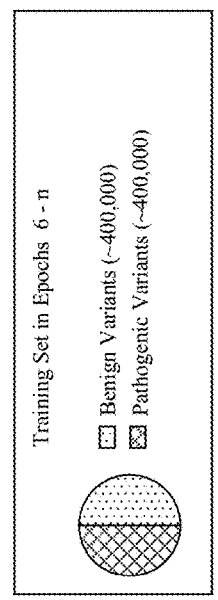
FIG. 8

Pathogenic/Unlabeled Missense Variant 1000

```
                1, 2, 3,    26,    49, 50, 51
1002R — Reference:   T C T ...... R ...... C H E           1002
                1, 2, 3,    26,    49, 50, 51
1002A — Alternative: T C T ...... W ...... C H E
```

Supplemental Benign Training Example

```
                1, 2, 3,    26,    49, 50, 51
1012R — Reference:   T C T ...... R ...... C H E           1012
                1, 2, 3,    26,    49, 50, 51
1012A — Alternative: T C T ...... R ...... C H E
```

Position Frequency Matrix Starting Point

| Amino Acid | 1 | 2 | 3 | ...... | 26 | ...... | 49 | 50 | 51 |
|---|---|---|---|---|---|---|---|---|---|
| I |   |   |   | ...... |   | ...... |   |   |   |
| L |   |   |   |   |   |   |   |   |   |
| V |   |   |   |   |   |   |   |   |   |
| F |   |   |   |   |   |   |   |   |   |
| M |   |   |   |   |   |   |   |   |   |
| C |   | 1 |   |   |   |   | 1 |   |   |
| A |   |   |   |   |   |   |   |   |   |
| G |   |   |   |   |   |   |   |   |   |
| P |   |   |   |   |   |   |   |   |   |
| T | 1 |   | 1 |   |   |   |   |   |   |
| S |   |   |   |   |   |   |   |   |   |
| Y |   |   |   |   |   |   |   |   |   |
| W |   |   |   |   |   |   |   |   |   |
| Q |   |   |   |   |   |   |   |   |   |
| N |   |   |   |   |   |   |   |   |   |
| H |   |   |   |   |   |   |   | 1 |   |
| E |   |   |   |   |   |   |   |   | 1 |
| D |   |   |   |   |   |   |   |   |   |
| K |   |   |   |   |   |   |   |   |   |
| R |   |   |   |   | 1 |   |   |   |   |

Benign Missense Variant     1100

1102R — Reference: positions 1, 2, 3, ... 26, ... 49, 50, 51 : T C T ...... R ...... C H E 1102A — Alternative: positions 1, 2, 3, ... 26, ... 49, 50, 51 : T C T ...... K ...... C H E

— 1102

Supplemental Benign Training Example

1112R — Reference: positions 1, 2, 3, ... 26, ... 49, 50, 51 : T C T ...... R ...... C H E 1112A — Alternative: positions 1, 2, 3, ... 26, ... 49, 50, 51 : T C T ...... R ...... C H E

— 1112

Position Frequency Matrix Starting Point

1122 — Amino Acid (rows: I, L, V, F, M, C, A, G, P, T, S, Y, W, Q, N, H, E, D, K, R) / Positions in Sequence: 1, 2, 3, ...... 26, ...... 49, 50, 51

- C: 1 at position 2; 1 at position 49
- T: 1 at position 1; 1 at position 3
- H: 1 at position 50
- E: 1 at position 51
- R: 1 at position 26

FIG. 11

Supplemental Benign Training Example 1300

Human Reference: $\underbrace{TCT}_{1,2,3,} \ldots \underbrace{R}_{26,} \ldots \underbrace{CHE}_{49,50,51}$

One Hot Encoded Human Reference
Positions in Sequence

| Amino Acid Encoding Row | 1 | 2 | 3 | ...... | 26 | ...... | 49 | 50 | 51 |
|---|---|---|---|---|---|---|---|---|---|
| I | 0 | 0 | 0 | | 0 | | 0 | 0 | 0 |
| L | 0 | 0 | 0 | | 0 | | 0 | 0 | 0 |
| V | 0 | 0 | 0 | | 0 | | 0 | 0 | 0 |
| F | 0 | 0 | 0 | | 0 | | 0 | 0 | 0 |
| M | 0 | 0 | 0 | | 0 | | 0 | 0 | 0 |
| C | 0 | 1 | 0 | | 0 | | 1 | 0 | 0 |
| A | 0 | 0 | 0 | | 0 | | 0 | 0 | 0 |
| G | 0 | 0 | 0 | | 0 | | 0 | 0 | 0 |
| P | 1 | 0 | 1 | | 0 | | 0 | 0 | 0 |
| T | 0 | 0 | 0 | | 0 | | 0 | 0 | 0 |
| S | 0 | 0 | 0 | | 0 | | 0 | 0 | 0 |
| Y | 0 | 0 | 0 | | 1 | | 0 | 0 | 0 |
| W | 0 | 0 | 0 | | 0 | | 0 | 0 | 0 |
| Q | 0 | 0 | 0 | | 0 | | 0 | 0 | 0 |
| N | 0 | 0 | 0 | | 0 | | 0 | 0 | 0 |
| H | 0 | 0 | 0 | | 0 | | 0 | 1 | 0 |
| E | 0 | 0 | 0 | | 0 | | 0 | 0 | 1 |
| D | 0 | 0 | 0 | | 0 | | 0 | 0 | 0 |
| K | 0 | 0 | 0 | | 0 | | 0 | 0 | 0 |
| R | 0 | 0 | 0 | | 1 | | 0 | 0 | 0 |

Human Alternative: $\underbrace{TCT}_{1,2,3,} \ldots \underbrace{R}_{26,} \ldots \underbrace{CHE}_{49,50,51}$

One Hot Encoded Human Alternate
Positions in Sequence

| Amino Acid Encoding Row | 1 | 2 | 3 | ...... | 26 | ...... | 49 | 50 | 51 |
|---|---|---|---|---|---|---|---|---|---|
| I | 0 | 0 | 0 | | 0 | | 0 | 0 | 0 |
| L | 0 | 0 | 0 | | 0 | | 0 | 0 | 0 |
| V | 0 | 0 | 0 | | 0 | | 0 | 0 | 0 |
| F | 0 | 0 | 0 | | 0 | | 0 | 0 | 0 |
| M | 0 | 0 | 0 | | 0 | | 0 | 0 | 0 |
| C | 0 | 1 | 0 | | 0 | | 1 | 0 | 0 |
| A | 0 | 0 | 0 | | 0 | | 0 | 0 | 0 |
| G | 0 | 0 | 0 | | 0 | | 0 | 0 | 0 |
| P | 0 | 0 | 0 | | 0 | | 0 | 0 | 0 |
| T | 1 | 0 | 1 | | 0 | | 0 | 0 | 0 |
| S | 0 | 0 | 0 | | 0 | | 0 | 0 | 0 |
| Y | 0 | 0 | 0 | | 1 | | 0 | 0 | 0 |
| W | 0 | 0 | 0 | | 0 | | 0 | 0 | 0 |
| Q | 0 | 0 | 0 | | 0 | | 0 | 0 | 0 |
| N | 0 | 0 | 0 | | 0 | | 0 | 0 | 0 |
| H | 0 | 0 | 0 | | 0 | | 0 | 1 | 0 |
| E | 0 | 0 | 0 | | 0 | | 0 | 0 | 1 |
| D | 0 | 0 | 0 | | 0 | | 0 | 0 | 0 |
| K | 0 | 0 | 0 | | 0 | | 0 | 0 | 0 |
| R | 0 | 0 | 0 | | 1 | | 0 | 0 | 0 |

FIG. 13

DEEP LEARNING-BASED TECHNIQUES FOR PRE-TRAINING DEEP CONVOLUTIONAL NEURAL NETWORKS

PRIORITY APPLICATIONS

This application is a continuation-in-part of U.S. Nonprovisional patent application Ser. No. 16/160,903, titled "DEEP LEARNING-BASED TECHNIQUES FOR TRAINING DEEP CONVOLUTIONAL NEURAL NETWORKS," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The non-provisional and provisional applications are hereby incorporated by reference for all purposes as if fully set forth herein.

This application is a continuation-in-part of U.S. Nonprovisional patent application Ser. No. 16/160,986, titled "DEEP CONVOLUTIONAL NEURAL NETWORKS FOR VARIANT CLASSIFICATION," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The non-provisional and provisional applications are hereby incorporated by reference for all purposes as if fully set forth herein.

This application is a continuation-in-part of U.S. Nonprovisional patent application Ser. No. 16/160,968, titled "SEMI-SUPERVISED LEARNING FOR TRAINING AN ENSEMBLE OF DEEP CONVOLUTIONAL NEURAL NETWORKS," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The non-provisional and provisional applications are hereby incorporated by reference for all purposes as if fully set forth herein.

This application is a continuation-in-part of PCT Patent Application No. PCT/US2018/55840, titled "DEEP LEARNING-BASED TECHNIQUES FOR TRAINING DEEP CONVOLUTIONAL NEURAL NETWORKS," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The PCT and provisional applications are hereby incorporated by reference for all purposes as if fully set forth herein.

This application is a continuation-in-part of PCT Patent Application No. PCT/US2018/55878, titled "DEEP CONVOLUTIONAL NEURAL NETWORKS FOR VARIANT CLASSIFICATION," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The PCT and provisional applications are hereby incorporated by reference for all purposes as if fully set forth herein.

This application is a continuation-in-part of PCT Patent Application No. PCT/US2018/55881, titled "SEMI-SUPERVISED LEARNING FOR TRAINING AN ENSEMBLE OF DEEP CONVOLUTIONAL NEURAL NETWORKS," filed on Oct. 15, 2018, which claims the benefit of US Provisional Patent Application Nos. 62/573,144, titled "TRAINING A DEEP PATHOGENICITY CLASSIFIER USING LARGE-SCALE BENIGN TRAINING DATA", filed Oct. 16, 2017; 62/573,149, titled "PATHOGENICITY CLASSIFIER BASED ON DEEP CONVOLUTIONAL NEURAL NETWORKS (CNNS)", filed Oct. 16, 2017; 62/573,153, titled "DEEP SEMI-SUPERVISED LEARNING THAT GENERATES LARGE-SCALE PATHOGENIC TRAINING DATA", filed Oct. 16, 2017; 62/582,898, titled "PATHOGENICITY CLASSIFICATION OF GENOMIC DATA USING DEEP CONVOLUTIONAL NEURAL NETWORKS (CNNs)", filed Nov. 7, 2017. The PCT and provisional applications are hereby incorporated by reference for all purposes as if fully set forth herein.

INCORPORATIONS

The following are incorporated by reference for all purposes as if fully set forth herein:

Document 1—A. van den Oord, S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

Document 2—S. Ö. Arik, M. Chrzanowski, A. Coates, G. Diamos, A. Gibiansky, Y. Kang, X. Li, J. Miller, A. Ng, J.

Raiman, S. Sengupta and M. Shoeybi, "DEEP VOICE: REAL-TIME NEURAL TEXT-TO-SPEECH," arXiv: 1702.07825, 2017;

Document 3—F. Yu and V. Koltun, "MULTI-SCALE CONTEXT AGGREGATION BY DILATED CONVOLUTIONS," arXiv: 1511.07122, 2016;

Document 4—K. He, X. Zhang, S. Ren, and J. Sun, "DEEP RESIDUAL LEARNING FOR IMAGE RECOGNITION," arXiv:1512.03385, 2015;

Document 5—R. K. Srivastava, K. Greff, and J. Schmidhuber, "HIGHWAY NETWORKS," arXiv: 1505.00387, 2015;

Document 6—G. Huang, Z. Liu, L. van der Maaten and K. Q. Weinberger, "DENSELY CONNECTED CONVOLUTIONAL NETWORKS," arXiv:1608.06993, 2017;

Document 7—C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

Document 8—S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

Document 9—J. M. Wolterink, T. Leiner, M. A. Viergever, and I. Isgum, "DILATED CONVOLUTIONAL NEURAL NETWORKS FOR CARDIOVASCULAR MR SEGMENTATION IN CONGENITAL HEART DISEASE," arXiv: 1704.03669, 2017;

Document 10—L. C. Piqueras, "AUTOREGRESSIVE MODEL BASED ON A DEEP CONVOLUTIONAL NEURAL NETWORK FOR AUDIO GENERATION," Tampere University of Technology, 2016;

Document 11—J. Wu, "Introduction to Convolutional Neural Networks," Nanjing University, 2017;

Document 12—I. J. Goodfellow, D. Warde-Farley, M. Mirza, A. Courville, and Y. Bengio, "CONVOLUTIONAL NETWORKS", Deep Learning, MIT Press, 2016; and Document 13—J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv:1512.07108, 2017.

Document 1 describes deep convolutional neural network architectures that use groups of residual blocks with convolution filters having same convolution window size, batch normalization layers, rectified linear unit (abbreviated ReLU) layers, dimensionality altering layers, atrous convolution layers with exponentially growing atrous convolution rates, skip connections, and a softmax classification layer to accept an input sequence and produce an output sequence that scores entries in the input sequence. The technology disclosed uses neural network components and parameters described in Document 1. In one implementation, the technology disclosed modifies the parameters of the neural network components described in Document 1. For instance, unlike in Document 1, the atrous convolution rate in the technology disclosed progresses non-exponentially from a lower residual block group to a higher residual block group. In another example, unlike in Document 1, the convolution window size in the technology disclosed varies between groups of residual blocks.

Document 2 describes details of the deep convolutional neural network architectures described in Document 1.

Document 3 describes atrous convolutions used by the technology disclosed. As used herein, atrous convolutions are also referred to as "dilated convolutions". Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

Document 4 describes residual blocks and residual connections used by the technology disclosed.

Document 5 describes skip connections used by the technology disclosed. As used herein, skip connections are also referred to as "highway networks".

Document 6 describes densely connected convolutional network architectures used by the technology disclosed.

Document 7 describes dimensionality altering convolution layers and modules-based processing pipelines used by the technology disclosed. One example of a dimensionality altering convolution is a 1×1 convolution.

Document 8 describes batch normalization layers used by the technology disclosed.

Document 9 also describes atrous/dilated convolutions used by the technology disclosed.

Document 10 describes various architectures of deep neural networks that can be used by the technology disclosed, including convolutional neural networks, deep convolutional neural networks, and deep convolutional neural networks with atrous/dilated convolutions.

Document 11 describes details of a convolutional neural network that can be used by the technology disclosed, including algorithms for training a convolutional neural network with subsampling layers (e.g., pooling) and fully-connected layers.

Document 12 describes details of various convolution operations that can be used by the technology disclosed.

Document 13 describes various architectures of convolutional neural networks that can be used by the technology disclosed.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep learning-based techniques for training deep convolutional neural networks. Particularly, the technology disclosed relates to pre-training deep convolutional neural networks to avoid overfitting.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Machine Learning

In machine learning input variables are used to predict an output variable. The input variables are often called features and are denoted by $X=(X_1, X_2, \ldots, X_k)$, where each $X_i$, $i \in 1, \ldots, k$ is a feature. The output variable is often called the response or dependent variable and is denoted by the variable $Y_i$. The relationship between Y and the corresponding X can be written in a general form:

$$Y = f(X) + \in$$

In the equation above, $f$ is a function of the features ($X_1$, $X_2, \ldots, X_k$) and $\in$ is the random error term. The error term is independent of X and has a mean value of zero.

In practice, the features X are available without having Y or knowing the exact relation between X and Y. Since the error term has a mean value of zero, the goal is to estimate $f$.

$$\hat{Y} = \hat{f} = (X)$$

In the equation above, $\hat{f}$ is the estimate of $\in$, which is often considered a black box, meaning that only the relation between the input and output of $\hat{f}$ is known, but the question why it works remains unanswered.

The function $\hat{f}$ is found using learning. Supervised learning and unsupervised learning are two ways used in machine learning for this task. In supervised learning, labeled data is used for training. By showing the inputs and the corresponding outputs (=labels), the function $\hat{f}$ is optimized such that it approximates the output. In unsupervised learning, the goal is to find a hidden structure from unlabeled data. The algorithm has no measure of accuracy on the input data, which distinguishes it from supervised learning.

Neural Networks

A neural network is a system of interconnected artificial neurons (e.g., $a_1$, $a_2$, $a_3$) that exchange messages between each other. The illustrated neural network has three inputs, two neurons in the hidden layer and two neurons in the output layer. The hidden layer has an activation function $f(\bullet)$ and the output layer has an activation function $g(\bullet)$. The connections have numeric weights (e.g., $w_{11}$, $w_{21}$, $w_{12}$, $w_{31}$, $w_{22}$, $w_{32}$, $v_{11}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

A neural network model is trained using training samples before using it used to predict outputs for production samples. The quality of predictions of the trained model is assessed by using a test set of training samples that is not given as input during training. If the model correctly predicts the outputs for the test samples then it can be used in inference with high confidence. However, if the model does not correctly predict the output for test samples then we can say that the model is overfitted on the training data and it has not been generalized on the unseen test data.

A survey of application of deep learning in genomics can be found in the following publications:

T. Ching et al., Opportunities And Obstacles For Deep Learning In Biology And Medicine, www.biorxiv.org: 142760, 2017;

Angermueller C, Parnamaa T, Parts L, Stegle O. Deep Learning For Computational Biology. Mol Syst Biol. 2016; 12:878;

Park Y, Kellis M. 2015 Deep Learning For Regulatory Genomics. Nat. Biotechnol. 33, 825-826. (doi:10.1038/nbt.3313);

Min, S., Lee, B. & Yoon, S. Deep Learning In Bioinformatics. Brief. Bioinform. bbw068 (2016);

Leung M K, Delong A, Alipanahi B et al. Machine Learning In Genomic Medicine: A Review of Computational Problems and Data Sets 2016; and Libbrecht M W, Noble W S. Machine Learning Applications In Genetics and Genomics. Nature Reviews Genetics 2015; 16(6):321-32.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 8 illustrates training of the pre-trained pathogenicity prediction model after the pre-training epochs.

FIG. 10 presents position frequency matrix starting point for an example amino acid sequence with pathogenic missense variant and corresponding supplemental benign training example.

FIG. 11 presents position frequency matrix starting point for an example amino acid sequence with benign missense variant and corresponding supplemental benign training example.

FIG. 13 presents example one hot encoding of a human reference amino acid sequence and a human alternative amino acid sequence.

DETAILED DESCRIPTION

Figure 1:
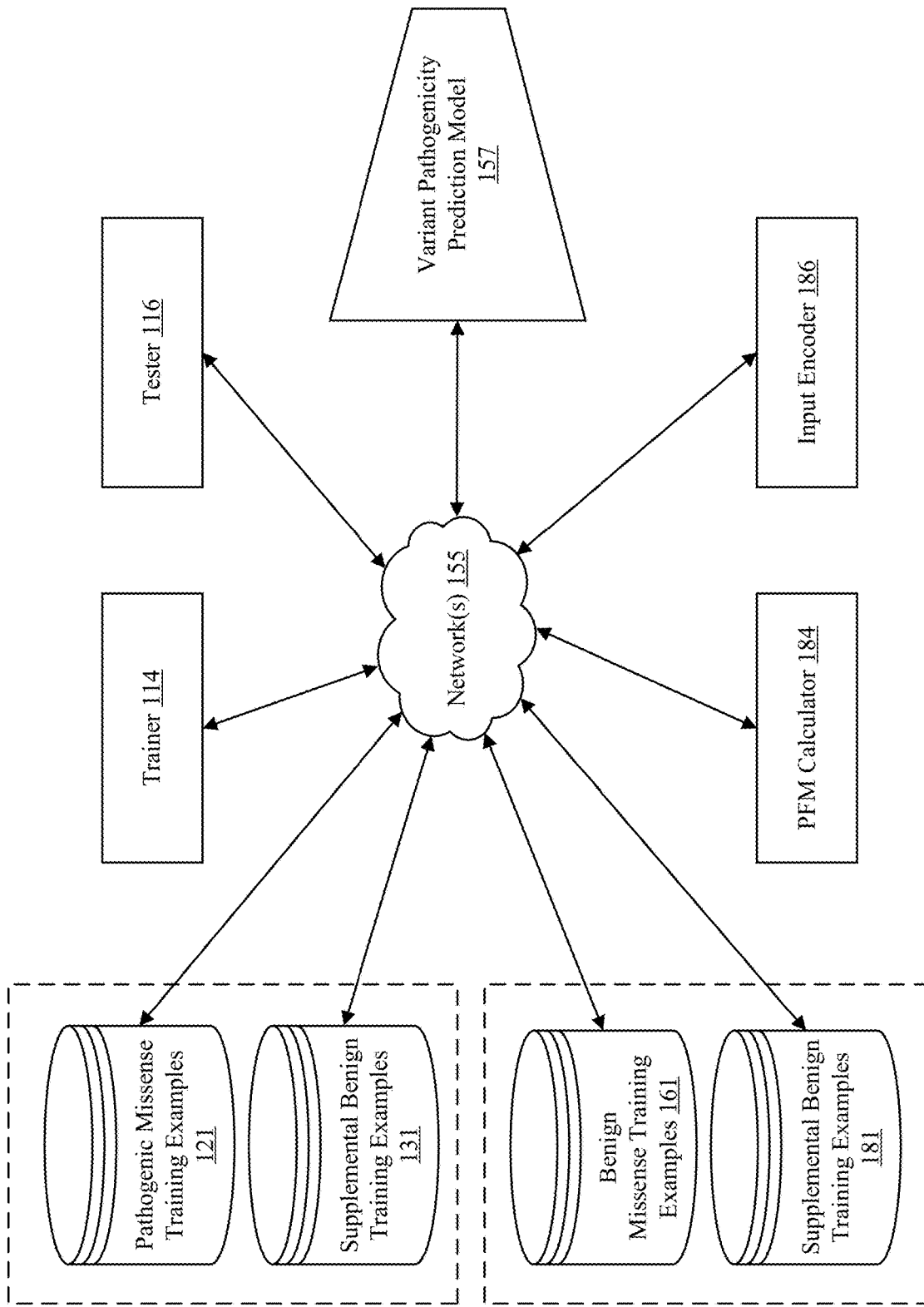
FIG. 1 illustrates an architectural level schematic of a system in which supplemental training examples are used to reduce overfitting during training of a variant pathogenicity prediction model.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

Sections of this application are repeated from the incorporated by reference applications to provide background for the improvement disclosed. The prior applications disclosed a deep learning system trained using non-human primate missense variant data, as explained below. Before providing background, we introduce the improvement disclosed.

The inventors observed, empirically, that some patterns of training sometimes cause the deep learning system to overemphasize a position frequency matrix input. Overfitting to the position frequency matrices could diminish the ability of the system to distinguish an amino acid missense that is typically benign, such as R→K, from an amino acid missense that typically is deleterious, such as R→W. Supplementing the training set with particularly chosen training examples can reduce or counteract overfitting and improve training outcomes.

Supplemental training examples, labelled benign, include the same position frequency matrices ("PFMs") as missense training examples, which may be unlabeled (and presumed pathogenic), labeled pathogenic, or labeled benign. The intuitive impact of these supplemental benign training examples is to force the backward propagation training to distinguish between the benign and pathogenic on a basis other than the position frequency matrix.

The supplemental benign training example is constructed to contrast against a pathogenic or unlabeled example in the training set. The supplemental benign training example could also reinforce a benign missense example. For contrast purposes, the pathogenic missense can be a curated pathogenic missense or it can be a combinatorially generated example in a training set. The chosen benign variant can be a synonymous variant, expressing the same amino acid from two different codons, two different trinucleotide sequences that code for the same amino acid. When a synonymous benign variant is used, it is not randomly constructed; instead, it is selected from synonymous variants observed in a sequenced population. The synonymous variant is likely to be a human variant, as more sequence data is available for humans than for other primates, mammals or vertebrates. Supplemental benign training examples have the same amino acid sequence in both reference and alternate amino acid sequences. Alternatively, the chosen benign variant can simply be at the same location as the training example against which it contrasts. This potentially can be as effective in counteracting overfitting as use of synonymous benign variants.

Use of the supplemental benign training examples can be discontinued after initial training epochs or can continue throughout training, as the examples accurately reflect nature.

Convolutional Neural Networks

As background, a convolutional neural network is a special type of neural network. The fundamental difference between a densely connected layer and a convolution layer is this. Dense layers learn global patterns in their input feature space, whereas convolution layers learn local patters: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere, for example, in the upper-left corner. A densely connected network would have to learn the pattern anew if it appeared at a new location. This makes convolutional neural networks data efficient because they need fewer training samples to learn representations that have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more subsampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels: red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

Figure 4:
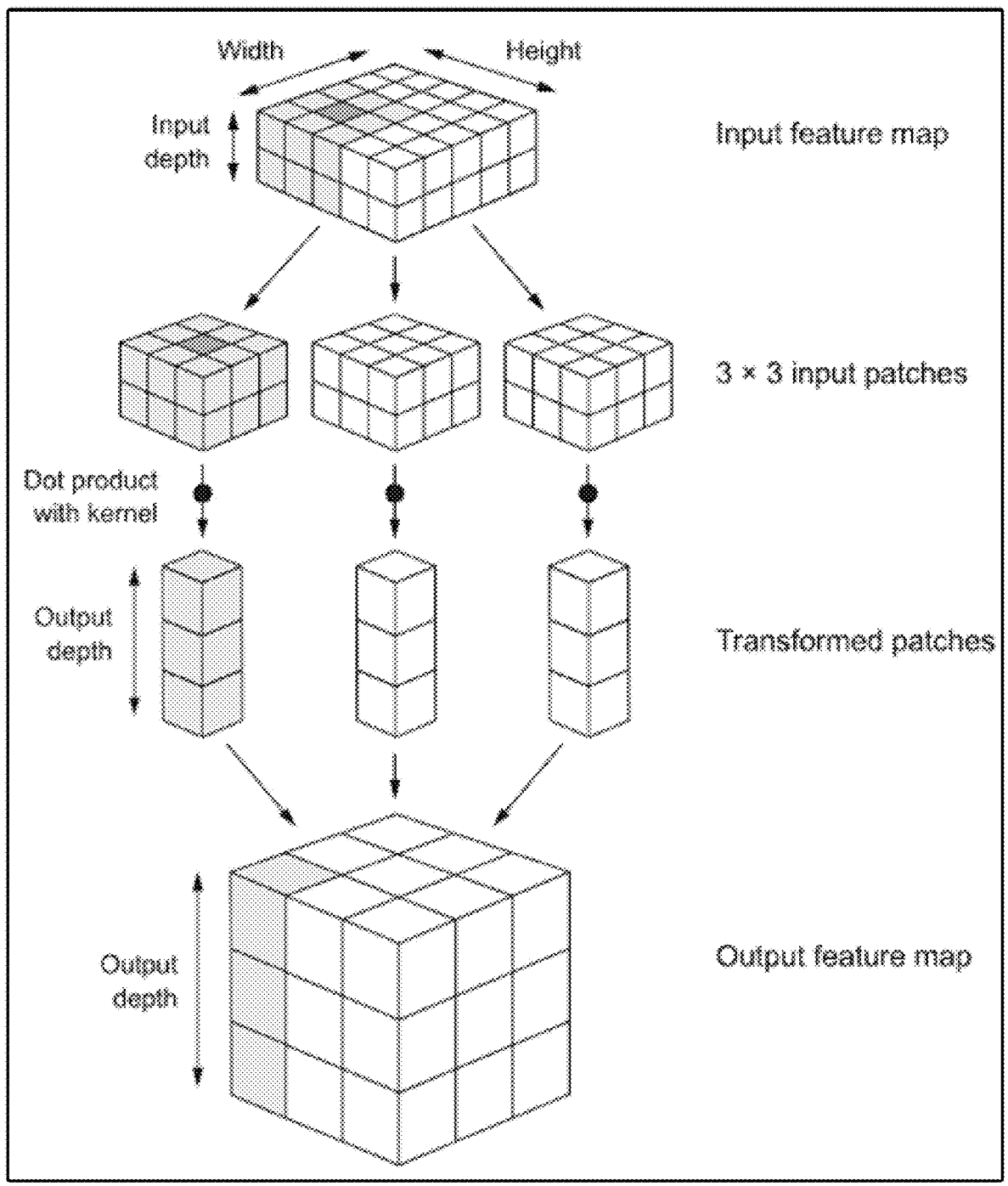
FIG. 4 depicts one implementation of workings of a convolutional neural network.

A convolution works by sliding these windows of size 3×3 or 5×5 over the 3D input feature map, stopping at every location, and extracting the 3D patch of surrounding features (shape (window_height, window_width, input depth)). Each such 3D patch is ten transformed (via a tensor product with the same learned weight matrix, called the convolution kernel) into a 1D vector of shape (output depth). All of these vectors are then spatially reassembled into a 3D output map of shape (height, width, output depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i−1: i+1, j−1:J+1, :]. The full process is detailed in FIG. 4 (labeled as 400).

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

Figure 5:
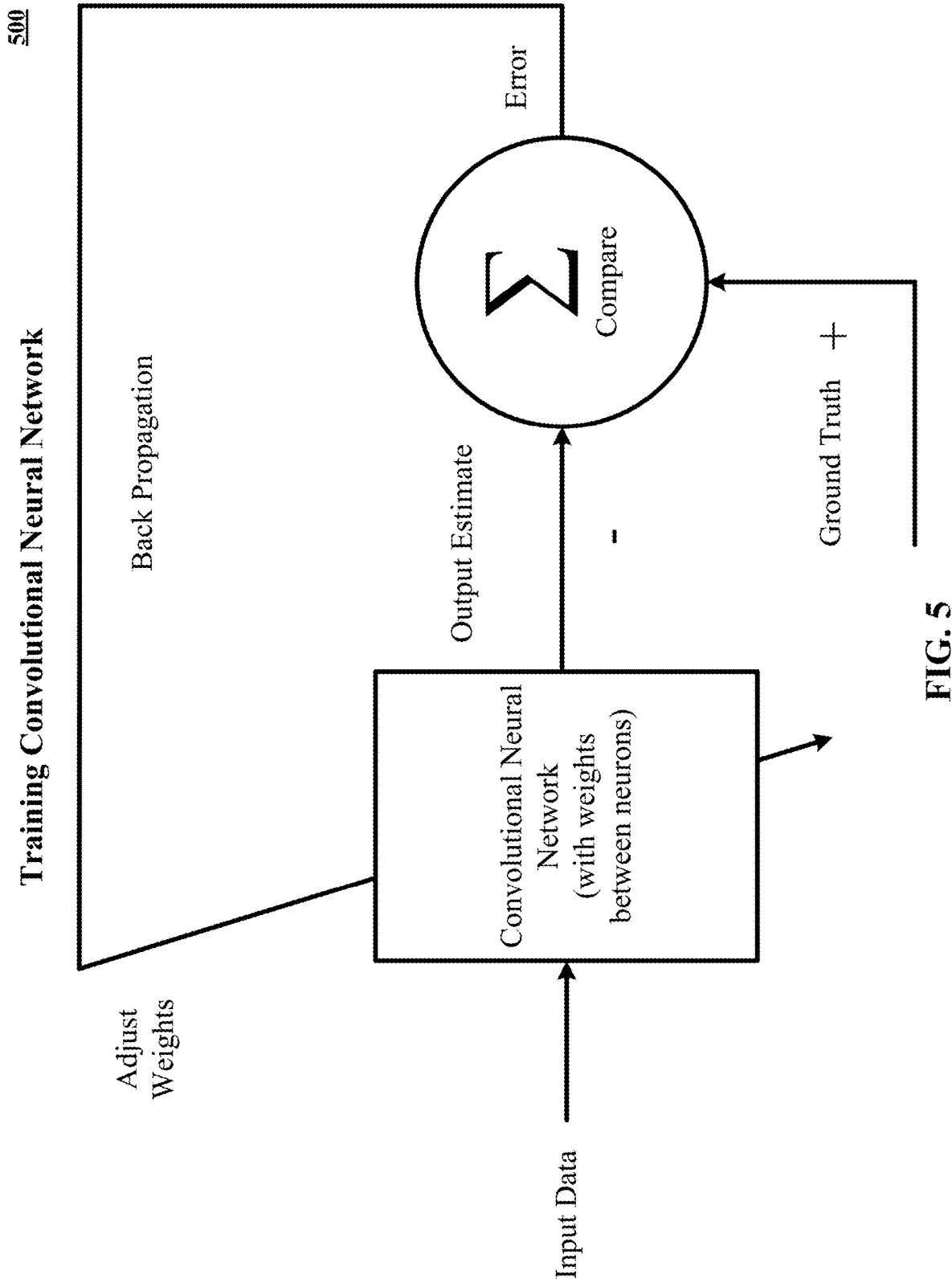
FIG. 5 depicts a block diagram of training a convolutional neural network in accordance with one implementation of the technology disclosed.

As further background, FIG. 5 depicts a block diagram 500 of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where δ=(ground truth)−(actual output)

In one implementation, the training rule is defined as:

$$w_{nm} \leftarrow w_{nm} + \alpha(t_m - \varphi_m)a_n$$

In the equation above: the arrow indicates an update of the value; $t_m$ is the target value of neuron m; $\varphi_m$ is the computed current output of neuron m; $a_n$ is input n; and α is the learning rate.

The intermediary step in the training includes generating a feature vector from the input data using the convolution layers. The gradient with respect to the weights in each layer, starting at the output is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1+e^{-h}}$$

In the sigmoid function above, h is the weighted sum computed by a neuron. The sigmoid function has the following derivative:

$$\frac{\partial \varphi}{\partial h} = \varphi(1-\varphi)$$

The algorithm includes computing the activation of all neurons in the network, yielding an output for the forward pass. The activation of neuron m in the hidden layers is described as:

$$\varphi_m = \frac{1}{1+e^{-h_m}}$$

$$h_m = \sum_{n=1}^{N} a_n w_{nm}$$

This is done for all the hidden layers to get the activation described as:

$$\varphi_k = \frac{1}{1+e^{h_k}}$$

$$h_k = \sum_{m=1}^{M} \varphi_m v_{mk}$$

Then, the error and the correct weights are calculated per layer. The error at the output is computed as:

$$\delta_{ok} = (t_k - \varphi_k)\varphi_k(1-\varphi_k)$$

The error in the hidden layers is calculated as:

$$\delta_{hm} = \varphi_m(1-\varphi_m)\sum_{k=1}^{K} v_{mk}\delta_{ok}$$

The weights of the output layer are updated as:

$$vmk \leftarrow vmk + \alpha \delta ok \varphi m$$

The weights of the hidden layers are updated using the learning rate α as:

$$vnm \leftarrow wnm + \alpha \delta hman$$

In one implementation, the convolutional neural network uses a gradient descent optimization to compute the error across all the layers. In such an optimization, for an input feature vector x and the predicted output ŷ, the loss function is defined as l for the cost of predicting ŷ when the target is y, i.e. l(ŷ, y). The predicted output ŷ is transformed from the input feature vector x using function $f$. Function $f$ is parameterized by the weights of convolutional neural network i.e. ŷ=$f_w$(x). The loss function is described as l(ŷ,y)= l($f_w$(x),y), or Q(z,w)=l($f_w$(x),y) where z is an input and output data pair (x, y). The gradient descent optimization is performed by updating the weights according to:

$$v_{t+1} = \mu v_t - \alpha \frac{1}{n} \sum_{i=1}^{N} \nabla w_t(z_t, w_t)$$

$$w_{t+1} = w_t + v_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $z_t$, described as:

$$v_{t+1} = \mu v - \alpha \nabla w Q(z_t, w_t)$$

$$w_{t+1} = w_t + v_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Additional disclosure and explanation of convolution layers, sub-sampling layers, and non-linear layers if found in the incorporated by reference applications, along with convolution examples and an explanation of training by backward propagation. Also covered in the incorporated by reference material are architectural variations on basic CNN technology.

One variation on the iterative balanced sampling described previously is selecting the entire elite training set in one or two cycles instead of twenty. There may be enough distinction, learned by semi-supervised training, between known benign training examples and reliably classified predicted pathogenic variants that just one or two training cycles, or three to five training cycles, may be sufficient to assemble the elite training set. Modification of the disclosed methods and devices to describe just one cycle or two cycles or a range of three to five cycles is hereby disclosed and can be readily accomplished by converting the previously disclosed iteration to a one or two or three to five cycles.

Deep Learning in Genomics

Some important contributions of the incorporated by reference applications are reiterated here. Genetic variations can help explain many diseases. Every human being has a unique genetic code and there are lots of genetic variants within a group of individuals. Most of the deleterious genetic variants have been depleted from genomes by natural selection. It is important to identify which genetic variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of variants remains a great challenge due to the complexity of cell type-specific transcription regulation systems.

Advances in biochemical technologies over the past decades have given rise to next generation sequencing (NGS) platforms that quickly produce genomic data at much lower costs than ever before. Such overwhelmingly large volumes of sequenced DNA remain difficult to annotate. Supervised machine learning algorithms typically perform well when large amounts of labeled data are available. In bioinformatics and many other data-rich disciplines, the process of labeling instances is costly; however, unlabeled instances are inexpensive and readily available. For a scenario in which the amount of labeled data is relatively small and the amount of unlabeled data is substantially larger, semi-supervised learning represents a cost-effective alternative to manual labeling.

An opportunity arises to use semi-supervised algorithms to construct deep learning-based pathogenicity classifiers that accurately predict pathogenicity of variants. Databases of pathogenic variants that are free from human ascertainment bias may result.

Regarding pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, a powerful computational model for predicting the pathogenicity of variants can have enormous benefits for both basic science and translational research.

Common polymorphisms represent natural experiments whose fitness has been tested by generations of natural selection. Comparing the allele frequency distributions for human missense and synonymous substitutions, we find that the presence of a missense variant at high allele frequencies in a non-human primate species reliably predicts that the variant is also under neutral selection in the human population. In contrast, common variants in more distant species experience negative selection as evolutionary distance increases.

We employ common variation from six non-human primate species to train a semi-supervised deep learning network that accurately classifies clinical de novo missense mutations using sequence alone. With over 500 known species, the primate lineage contains sufficient common variation to systematically model the effects of most human variants of unknown significance.

The human reference genome harbors more than 70 million potential protein-altering missense substitutions, the vast majority of which are rare mutations whose effects on human health have not been characterized. These variants of unknown significance present a challenge for genome interpretation in clinical applications, and are a roadblock to the long term adoption of sequencing for population-wide screening and individualized medicine.

Cataloguing common variation across diverse human populations is an effective strategy for identifying clinically benign variation, but the common variation available in modern day humans is limited by bottleneck events in our species' distant past. Humans and chimpanzees share 99% sequence identity, suggesting that natural selection operating on chimpanzee variants has the potential to model the effects of variants that are identical-by-state in human. The mean coalescence time for neutral polymorphisms in the human population is a fraction of the species' divergence time, hence, naturally occurring chimpanzee variation largely explores mutational space that is non-overlapping with human variation, aside from rare instances of haplotypes maintained by balancing selection.

The recent availability of aggregated exome data from 60,706 humans enables us to test this hypothesis by comparing the allele frequency spectra for missense and synonymous mutations. Singleton variants in ExAC closely match the expected 2.2:1 missense:synonymous ratio predicted by de novo mutation after adjusting for mutational rate using trinucleotide context, but at higher allele frequencies the number of observed missense variants decreases due to the filtering out of deleterious variants by natural selection. The pattern of missense:synonymous ratios across the allele frequency spectrum indicates that a large fraction of missense variants with population frequency <0.1% are mildly deleterious, that is, neither pathogenic enough to warrant immediate removal from the population, nor neutral enough to be allowed to exist at high allele frequencies, consistent with prior observations on more limited population data. These findings support the widespread empirical practice by diagnostic labs of filtering out variants with greater than 0.10/%1% allele frequency as likely benign for penetrant genetic disease, aside from a handful of well-documented exceptions caused by balancing selection and founder effects.

Repeating this analysis with the subset of human variants that are identical-by-state with common chimpanzee variants (observed more than once in chimpanzee population sequencing), we find that the missense:synonymous ratio is largely constant across the allele frequency spectrum. The high allele frequency of these variants in the chimpanzee population indicates that they have already been through the sieve of natural selection in chimpanzee, and their neutral impact on fitness in human populations provides compelling evidence that the selective pressures on missense variants are highly concordant in the two species. The lower missense:synonymous ratio observed in chimpanzee is consistent with the larger effective population size in ancestral chimpanzee populations enabling more efficient filtering of mildly deleterious variants.

In contrast, rare chimpanzee variants (observed only once in chimpanzee population sequencing) show a modest decrease in missense:synonymous ratio at higher allele frequencies. Simulating an identically sized cohort from human variation data, we estimate that only 64% of the variants observed once in a cohort of this size would have an allele frequency greater than 0.1% in the general population, compared to 99.8% for the variants seen multiple times in the cohort, indicating that not all of the rare chimpanzee variants have been through the sieve of selection. Overall, we estimate that 16% of the ascertained chimpanzee missense variants have an allele frequency less than 0.1% in the general population, and would be subject to negative selection at higher allele frequencies.

We next characterize human variants that are identical-by-state with variation observed in other non-human primate species (Bonobo, Gorilla, Orangutan, Rhesus, and Marmoset). Similar to chimpanzee, we observe that the missense:synonymous ratios are roughly equivalent across the allele frequency spectrum, other than a slight depletion of missense variation at high allele frequencies, which would be anticipated due to the inclusion of a small number of rare variants (~5-15%). These results imply that the selective forces on missense variants are largely concordant within the primate lineage at least out to new world monkeys, which are estimated to have diverged from the human ancestral lineage ~35 million years ago.

Human missense variants that are identical-by-state with variants in other primates are strongly enriched for benign consequence in ClinVar. After excluding variants with unknown or conflicting annotations, we observe that human variants with primate orthologs are approximately 95% likely to be annotated as Benign or Likely Benign in ClinVar, compared to 45% for missense variation in general. The small fraction of ClinVar variants that are classified as pathogenic from non-human primates is comparable to the fraction of pathogenic ClinVar variants that would be observed by ascertaining rare variants from a similar sized cohort of healthy humans. A substantial fraction of these variants annotated as Pathogenic or Likely Pathogenic indicate that received their classifications prior to the advent of large allele frequency databases, and might be curated differently today.

The field of human genetics has long relied upon model organisms to infer the clinical impact of human mutations, but the long evolutionary distance to most genetically tractable animal models raises concerns about the extent to which these findings are generalizable back to human. To examine the concordance of natural selection on missense variants in human and more distant species, we extend our analysis beyond the primate lineage to include largely common variation from four additional mammalian species (mouse, pig, goat, cow) and two species of more distant vertebrates (chicken, zebrafish). In contrast to the prior primate analyses, we observe that missense variation is markedly depleted at common allele frequencies compared to rare allele frequencies, especially at greater evolutionary distances, indicating that a substantial fraction of common missense variation in more distant species would experience negative selection in human populations. Nonetheless, the observation of a missense variant in more distant vertebrates still increases the likelihood of benign consequence, as the fraction of common missense variants depleted by natural selection is far less than the ~50% depletion for human missense variants at baseline. Consistent with these results, we find that human missense variants that have been observed in mouse, dog, pig, and cow are approximately 85% likely to be annotated as Benign or Likely Benign in ClinVar, compared to 95% for primate variation and 45% for the ClinVar database as a whole.

The presence of closely related pairs of species at varying evolutionary distances also provides an opportunity to evaluate the functional consequences of fixed missense substitutions in human populations. Within closely related pairs of species (branch length<0.1) on the mammalian family tree, we observe that fixed missense variation is depleted at common allele frequencies compared to rare allele frequencies, indicating that a substantial fraction of inter-species fixed substitutions would be non-neutral in human, even within the primate lineage. A comparison of the magnitude of missense depletion indicates that inter-species fixed substitutions are significantly less neutral than within-species polymorphisms. Intriguingly, inter-species variation between closely related mammals are not substantially more pathogenic in ClinVar (83% likely to be annotated as Benign or Likely Benign) compared to within-species common polymorphisms, suggesting that these changes do not abrogate protein function, but rather reflect tuning of protein function that confer species-specific adaptive advantages.

The large number of possible variants of unknown significance and the crucial importance of accurate variant classification for clinical applications has inspired multiple attempts to tackle the problem with machine learning, but these efforts have largely been limited by the insufficient quantity of common human variants and the dubious quality of annotations in curated databases. Variation from the six non-human primates contributes over 300,000 unique missense variants that are non-overlapping with common human variation and largely of benign consequence, greatly enlarging the size of the training dataset that can be used for machine learning approaches.

Unlike earlier models which employ a large number of human-engineered features and meta-classifiers, we apply a simple deep learning residual network which takes as input only the amino acid sequence flanking the variant of interest and the orthologous sequence alignments in other species. To provide the network with information about protein structure, we train two separate networks to learn secondary structure and solvent accessibility from sequence alone, and incorporate these as sub-networks in the larger deep learning network to predict effects on protein structure. Using sequence as a starting point avoids potential biases in protein structure and functional domain annotation, which may be incompletely ascertained or inconsistently applied.

We use semi-supervised learning to overcome the problem of the training set containing only variants with benign labels, by initially training an ensemble of networks to separate likely benign primate variants versus random unknown variants that are matched for mutation rate and sequencing coverage. This ensemble of networks is used to score the complete set of unknown variants and influence the selection of unknown variants to seed the next iteration of the classifier by biasing towards unknown variants with more pathogenic predicted consequence, taking gradual steps at each iteration to prevent the model from prematurely converging to a suboptimal result.

Common primate variation also provides a clean validation dataset for evaluating existing methods that is completely independent of previously used training data, which has been hard to evaluate objectively because of the proliferation of meta-classifiers. We evaluated the performance of our model, along with four other popular classification algorithms (Sift, Polyphen2, CADD, M-CAP), using 10,000 held-out primate common variants. Because roughly 50% of all human missense variants would be removed by natural selection at common allele frequencies, we calculated the 50th-percentile score for each classifier on a set of randomly picked missense variants that were matched to the 10,000 held-out primate common variants by mutational rate, and used that threshold to evaluate the held-out primate common variants. The accuracy of our deep learning model was significantly better than the other classifiers on this independent validation dataset, using either deep learning networks that were trained only on human common variants, or using both human common variants and primate variants.

Recent trio sequencing studies have catalogued thousands of de novo mutations in patients with neurodevelopmental disorders and their healthy siblings, enabling assessment of the strength of various classification algorithms in separating de novo missense mutations in cases versus controls. For each of the four classification algorithms, we scored each de novo missense variant in cases versus controls, and report the p-value from the Wilcoxon rank-sum test of the difference between the two distributions, showing that the deep learning method trained on primate variants ($p\sim10^{-33}$) performed far better than the other classifiers ($p\sim10^{13}$ to $10^{-19}$) on this clinical scenario. From the ~1.3-fold enrichment of de novo missense variants over expectation previously reported for this cohort, and prior estimates that ~20% of missense variants produce loss-of-function effects, we would expect a perfect classifier to separate the two classes with a p-value of $p\sim10^{-40}$.

The accuracy of the deep learning classifier scales with the size of the training dataset, and variation data from each of the six primate species independently contributes to boosting the accuracy of the classifier. The large number and diversity of extant non-human primate species, along with evidence showing that the selective pressures on protein-altering variants are largely concordant within the primate lineage, suggests systematic primate population sequencing as an effective strategy to classify the millions of human variants of unknown significance that currently limit clinical genome interpretation. Of the 504 known non-human primate species, roughly 60% face extinction due to hunting and habitat loss, motivating urgency for a worldwide conservation effort that would benefit both these unique and irreplaceable species and our own.

Although not as much aggregate whole genome data is available as exome data, limiting the power to detect the impact of natural selection in deep intronic regions, we were also able to calculate the observed vs expected counts of cryptic splice mutations far from exonic regions. Overall, we observe a 60% depletion in cryptic splice mutations at a distance >50 nt from an exon-intron boundary. The attenuated signal is likely a combination of the smaller sample size with whole genome data compared to exome, and the greater difficulty of predicting the impact of deep intronic variants.

Terminology

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

A base refers to a nucleotide base or nucleotide, A (adenine), C (cytosine), T (thymine), or G (guanine).

This application uses the terms "protein" and "translated sequence" interchangeably.

This application uses the terms "codon" and "base triplet" interchangeably.

This application uses the terms "amino acid" and "translated unit" interchangeably.

This application uses the phrases "variant pathogenicity classifier", "convolutional neural network-based classifier for variant classification", and "deep convolutional neural network-based classifier for variant classification" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual.

The term "read" refers to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed).

The term "variant" refers to a nucleic acid sequence that is different from a nucleic acid reference. Typical nucleic acid sequence variants include without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on the number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-20 inversely proportional to the probability that a single sequenced base is correct. For example, a T base call with Q of 20 is considered likely correct with a confidence P-value of 0.01. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Sequencing Process

This section provides background on sequencing by synthesis (SBS) and identification of variants. Implementations set forth herein may be applicable to analyzing nucleic acid sequences to identify sequence variations. Implementations may be used to analyze potential variants/alleles of a genetic position/locus and determine a genotype of the genetic locus or, in other words, provide a genotype call for the locus. By way of example, nucleic acid sequences may be analyzed in accordance with the methods and systems described in US Patent Application Publication No. 2016/0085910 and US Patent Application Publication No. 2013/0296175, the complete subject matter of which are expressly incorporated by reference herein in their entirety.

In one implementation, a sequencing process includes receiving a sample that includes or is suspected of including nucleic acids, such as DNA. The sample may be from a known or unknown source, such as an animal (e.g., human), plant, bacteria, or fungus. The sample may be taken directly from the source. For instance, blood or saliva may be taken directly from an individual. Alternatively, the sample may not be obtained directly from the source. Then, one or more processors direct the system to prepare the sample for sequencing. The preparation may include removing extraneous material and/or isolating certain material (e.g., DNA). The biological sample may be prepared to include features for a particular assay. For example, the biological sample may be prepared for sequencing-by-synthesis (SBS). In certain implementations, the preparing may include amplification of certain regions of a genome. For instance, the preparing may include amplifying predetermined genetic loci that are known to include STRs and/or SNPs. The genetic loci may be amplified using predetermined primer sequences.

Next, the one or more processors may direct the system to sequence the sample. The sequencing may be performed through a variety of known sequencing protocols. In particular implementations, the sequencing includes SBS. In SBS, a plurality of fluorescently-labeled nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders.

The nucleic acids can be prepared such that they comprise a known primer sequence that is adjacent to an unknown target sequence. To initiate the first SBS sequencing cycle, one or more differently labeled nucleotides, and DNA polymerase, etc., can be flowed into/through the flow cell by a fluid flow subsystem. Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g., A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection operations can be repeated several times to complete a sequencing run. Example sequencing methods are described, for example, in Bentley et al., Nature 456:53-59 (2008), International Publication No. WO 04/018497; U.S. Pat. No. 7,057,026; International Publication No. WO 91/06678; International Publication No. WO 07/123744; U.S. Pat. Nos. 7,329,492; 7,211,414; 7,315,019; 7,405,281, and U.S. Patent Application Publication No. 2008/0108082, each of which is incorporated herein by reference.

In some implementations, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Application Publication No. 2002/0055100; U.S. Pat. No. 7,115,400; U.S. Patent Application Publication No. 2004/0096853; U.S. Patent Application Publication No. 2004/0002090; U.S. Patent Application Publication No. 2007/0128624; and U.S. Patent Application Publication No. 2008/0009420, each of which is incorporated herein by reference in its entirety. Another useful method for amplifying nucleic acids on a surface is rolling circle amplification (RCA), for example, as described in Lizardi et al., Nat. Genet. 19:225-232 (1998)

and U.S. Patent Application Publication No. 2007/0099208 A1, each of which is incorporated herein by reference.

One example SBS protocol exploits modified nucleotides having removable 3' blocks, for example, as described in International Publication No. WO 04/018497, U.S. Patent Application Publication No. 2007/0166705A1, and U.S. Pat. No. 7,057,026, each of which is incorporated herein by reference. For example, repeated cycles of SBS reagents can be delivered to a flow cell having target nucleic acids attached thereto, for example, as a result of the bridge amplification protocol. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, Mass., USA, part number M5505S), by exposure to heat or alkali, cleavage of ribonucleotides incorporated into amplification products otherwise comprised of deoxyribonucleotides, photochemical cleavage or cleavage of a peptide linker. After the linearization operation a sequencing primer can be delivered to the flow cell under conditions for hybridization of the sequencing primer to the target nucleic acids that are to be sequenced.

A flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'-OH group available to direct further sequence extension and therefore the polymerase cannot add further nucleotides. The SBS extension reagent can be removed and replaced with scan reagent containing components that protect the sample under excitation with radiation. Example components for scan reagent are described in U.S. Patent Application Publication No. 2008/0280773 A1 and U.S. patent application Ser. No. 13/018,255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Example deblock reagents that are useful for respective blocking groups are described in WO004018497, US 2007/0166705A1 and U.S. Pat. No. 7,057,026, each of which is incorporated herein by reference. The deblock reagent can be washed away leaving target nucleic acids hybridized to extended primers having 3'-OH groups that are now competent for addition of a further nucleotide. Accordingly the cycles of adding extension reagent, scan reagent, and deblock reagent, with optional washes between one or more of the operations, can be repeated until a desired sequence is obtained. The above cycles can be carried out using a single extension reagent delivery operation per cycle when each of the modified nucleotides has a different label attached thereto, known to correspond to the particular base. The different labels facilitate discrimination between the nucleotides added during each incorporation operation. Alternatively, each cycle can include separate operations of extension reagent delivery followed by separate operations of scan reagent delivery and detection, in which case two or more of the nucleotides can have the same label and can be distinguished based on the known order of delivery.

Although the sequencing operation has been discussed above with respect to a particular SBS protocol, it will be understood that other protocols for sequencing any of a variety of other molecular analyses can be carried out as desired.

Then, the one or more processors of the system receive the sequencing data for subsequent analysis. The sequencing data may be formatted in various manners, such as in a .BAM file. The sequencing data may include, for example, a number of sample reads. The sequencing data may include a plurality of sample reads that have corresponding sample sequences of the nucleotides. Although only one sample read is discussed, it should be understood that the sequencing data may include, for example, hundreds, thousands, hundreds of thousands, or millions of sample reads. Different sample reads may have different numbers of nucleotides. For example, a sample read may range between 10 nucleotides to about 500 nucleotides or more. The sample reads may span the entire genome of the source(s). As one example, the sample reads are directed toward predetermined genetic loci, such as those genetic loci having suspected STRs or suspected SNPs.

Each sample read may include a sequence of nucleotides, which may be referred to as a sample sequence, sample fragment or a target sequence. The sample sequence may include, for example, primer sequences, flanking sequences, and a target sequence. The number of nucleotides within the sample sequence may include 30, 40, 50, 60, 70, 80, 90, 100 or more. In some implementations, one or more of the sample reads (or sample sequences) includes at least 150 nucleotides, 200 nucleotides, 300 nucleotides, 400 nucleotides, 500 nucleotides, or more. In some implementations, the sample reads may include more than 1000 nucleotides, 2000 nucleotides, or more. The sample reads (or the sample sequences) may include primer sequences at one or both ends.

Next, the one or more processors analyze the sequencing data to obtain potential variant call(s) and a sample variant frequency of the sample variant call(s). The operation may also be referred to as a variant call application or variant caller. Thus, the variant caller identifies or detects variants and the variant classifier classifies the detected variants as somatic or germline. Alternative variant callers may be utilized in accordance with implementations herein, wherein different variant callers may be used based on the type of sequencing operation being performed, based on features of the sample that are of interest and the like. One non-limiting example of a variant call application, such as the Pisces™ application by Illumina Inc. (San Diego, Calif.) hosted at https://github.com/Illumina/Pisces and described in the article Dunn, Tamsen & Berry, Gwenn & Emig-Agius, Dorothea & Jiang, Yu & Iyer, Anita & Udar, Nitin & Strömberg, Michael. (2017). Pisces: An Accurate and Versatile Single Sample Somatic and Germline Variant Caller. 595-595. 10.1145/3107411.3108203, the complete subject matter of which is expressly incorporated herein by reference in its entirety.

Benign Training Set Generation

Generation of expanded training sets is disclosed in the incorporated by reference applications. Millions of human genomes and exomes have been sequenced, but their clinical applications remain limited due to the difficulty of distinguishing disease-causing mutations from benign genetic variation. Here we demonstrate that common missense variants in other primate species are largely clinically benign in human, enabling pathogenic mutations to be systematically identified by the process of elimination. Using hundreds of thousands of common variants from population sequencing of six non-human primate species, we train a deep neural network that identifies pathogenic mutations in rare disease patients with 88% accuracy and enables the discovery of 14 new candidate genes in intellectual disability at genome-wide significance. Cataloging common variation from additional primate species would improve interpretation for millions of variants of uncertain significance, further advancing the clinical utility of human genome sequencing.

The clinical actionability of diagnostic sequencing is limited by the difficulty of interpreting rare genetic variants in human populations and inferring their impact on disease risk. Because of their deleterious effects on fitness, clinically significant genetic variants tend to be extremely rare in the population and, for the vast majority, their effects on human health have not been determined. The large number and rarity of these variants of uncertain clinical significance present a formidable obstacle to the adoption of sequencing for individualized medicine and population-wide health screening.

Most penetrant Mendelian diseases have very low prevalence in the population, hence the observation of a variant at high frequencies in the population is strong evidence in favor of benign consequence. Assaying common variation across diverse human populations is an effective strategy for cataloguing benign variants, but the total amount of common variation in present-day humans is limited due to bottleneck events in our species' recent history, during which a large fraction of ancestral diversity was lost. Population studies of present-day humans show a remarkable inflation from an effective population size ($N_e$) of less than 10,000 individuals within the last 15,000-65,000 years, and the small pool of common polymorphisms traces back to the limited capacitance for variation in a population of this size. Out of more than 70 million potential protein-altering missense substitutions in the reference genome, only roughly 1 in 1,000 are present at greater than 0.1% overall population allele frequency.

Outside of modern human populations, chimpanzees comprise the next closest extant species, and share 99.4% amino acid sequence identity. The near-identity of the protein-coding sequence in humans and chimpanzees suggests that purifying selection operating on chimpanzee protein-coding variants might also model the consequences on fitness of human mutations that are identical-by-state.

Because the mean time for neutral polymorphisms to persist in the ancestral human lineage (~$4N_e$ generations) is a fraction of the species' divergence time (~6 million years ago), naturally occurring chimpanzee variation explores mutational space that is largely non-overlapping except by chance, aside from rare instances of haplotypes maintained by balancing selection. If polymorphisms that are identical-by-state similarly affect fitness in the two species, the presence of a variant at high allele frequencies in chimpanzee populations should indicate benign consequence in human, expanding the catalog of known variants whose benign consequence has been established by purifying selection. Substantial additional detail is given in the incorporated by reference applications.

Architecture of the Deep Learning Network

In one implementation disclosed by the incorporated by reference applications, the pathogenicity prediction network takes as input the 51-length amino acid sequence centered at the variant of interest, and the outputs of the secondary structure and solvent accessibility networks (FIG. 2 and FIG. 3) with the missense variant substituted in at the central position. Three 51-length position frequency matrices are generated from multiple sequence alignments of 99 vertebrates, including one for 11 primates, one for 50 mammals excluding primates, and one for 38 vertebrates excluding primates and mammals.

The secondary structure deep learning network predicts a three-state secondary structure at each amino acid position: alpha helix (H), beta sheet (B), and coils (C). The solvent accessibility network predicts a three-state solvent accessibility at each amino acid position: buried (B), intermediate (I), and exposed (E). Both networks can only take the flanking amino acid sequence as their inputs, and can be trained using labels from known non-redundant crystal structures in the Protein DataBank. For the input to the pretrained three-state secondary structure and three-state solvent accessibility networks, a single length position frequency matrix, which is generated from the multiple sequence alignments for all 99 vertebrates, also with length 51 and depth 20, can be used. After pre-training the networks on known crystal structures from the Protein DataBank, the final two layers for the secondary structure and solvent models can be removed and the output of the network can be directly connected to the input of the pathogenicity model. Exemplary testing accuracy achieved for the three-state secondary structure prediction model was 79.86%. There was no substantial difference when comparing the predictions of the neural network when using DSSP-annotated structure labels for the approximately ~4,000 human proteins that had crystal structures versus using predicted structure labels only.

Both our deep learning network for pathogenicity prediction (PrimateAI) and deep learning networks for predicting secondary structure and solvent accessibility adopted the architecture of residual blocks. The detailed architecture for PrimateAI is described in FIG. 3.

Figure 2:
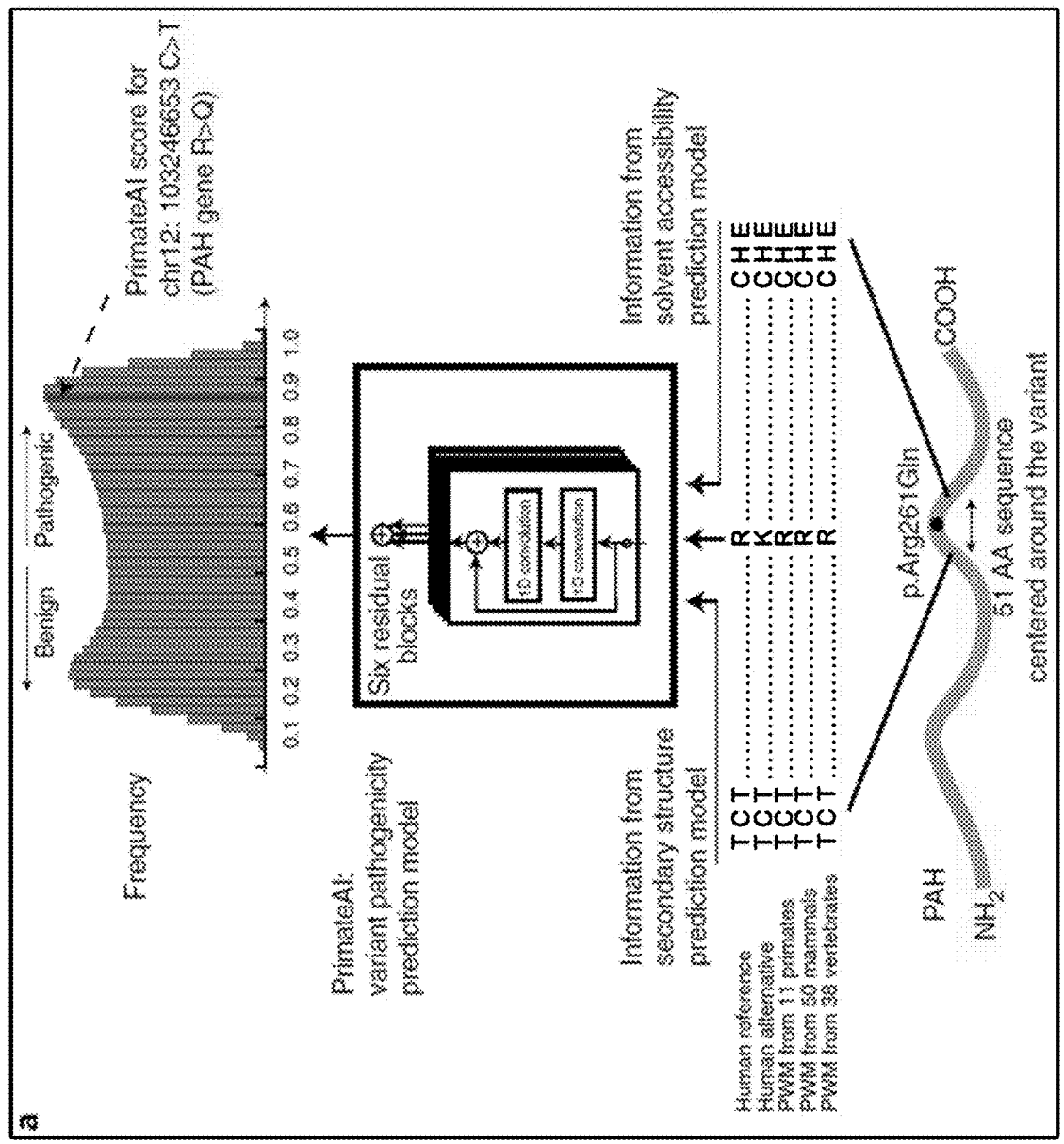
FIG. 2 shows an example architecture of a deep residual network for pathogenicity prediction, referred to herein as "PrimateAI".

FIG. 2 shows an example architecture 200 of a deep residual network for pathogenicity prediction, referred to herein as "PrimateAI". In FIG. 2, 1D refers to 1-dimensional convolutional layer. Predicted pathogenicity is on a scale from 0 (benign) to 1 (pathogenic). The network takes as input the human amino acid (AA) reference and alternate sequence (51 AAs) centered at the variant, the position weight matrix (PWM) conservation profiles calculated from 99 vertebrate species, and the outputs of secondary structure and solvent accessibility prediction deep learning networks, which predict three-state protein secondary structure (helix—H, beta sheet—B, and coil—C) and three-state solvent accessibility (buried—B, intermediate—I, and exposed—E).

Figure 3:
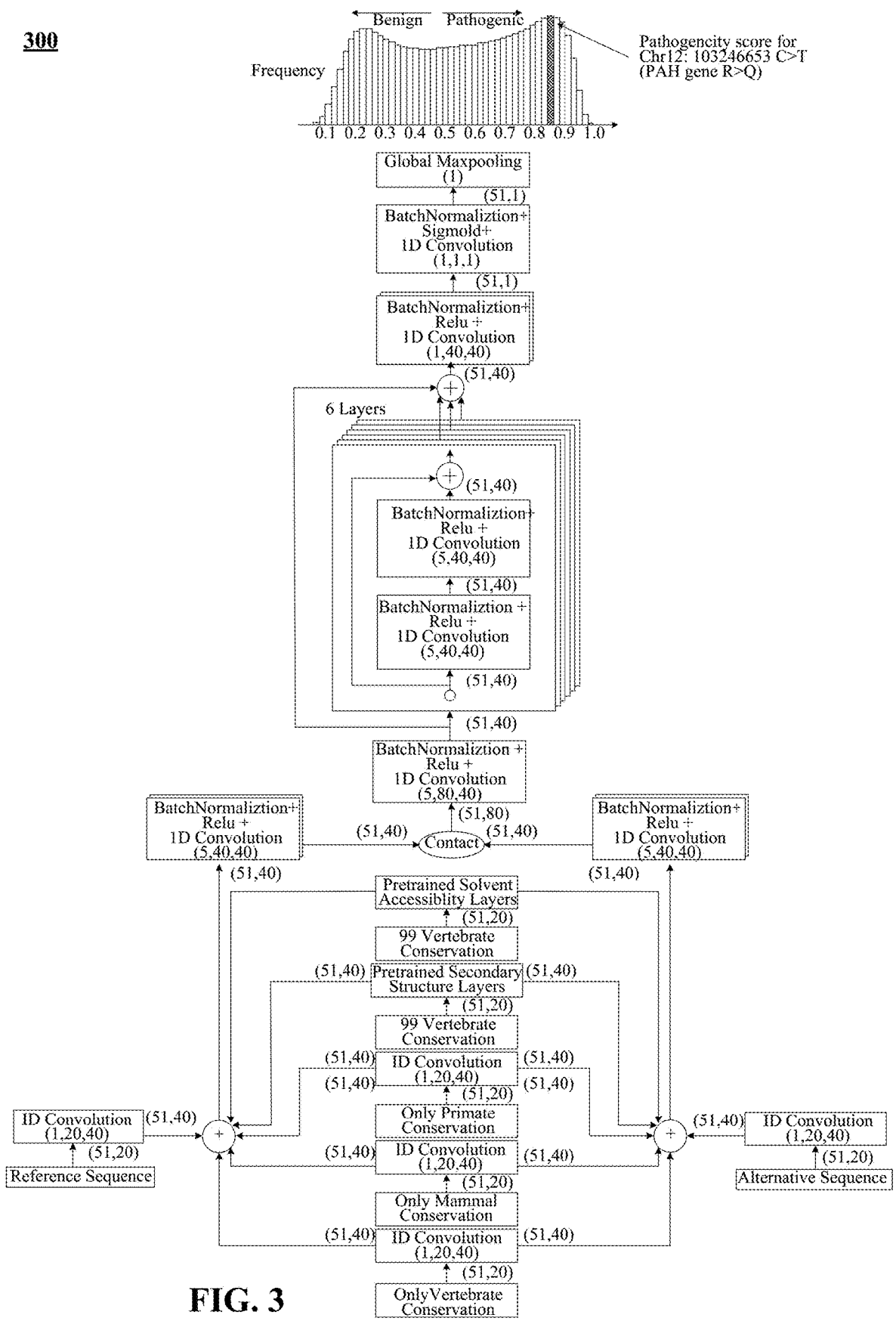
FIG. 3 depicts a schematic illustration of PrimateAI, the deep learning network architecture for pathogenicity classification.

FIG. 3 depicts a schematic illustration 300 of PrimateAI, the deep learning network architecture for pathogenicity classification. The inputs to the model include 51 amino acids (AA) of flanking sequence for both the reference sequence and the sequence with the variant substituted in, conservation represented by three 51-AA-length position-weighted matrices from primate, mammal, and vertebrate alignments, and the outputs of pre-trained secondary structure network and solvent accessibility network (also 51 AA in length).

Improvement by Pre-Training

This disclosure introduces pre-training a pathogenicity prediction model to reduce or counteract overfitting and improve training outcomes. The system is described with reference to FIG. 1 showing an architectural level schematic 100 of the system in accordance with an implementation.

Because FIG. 1 is an architectural diagram, certain details are intentionally omitted to improve the clarity of description. The discussion of FIG. 1 is organized as follows. First, the elements of the figure are described, followed by their interconnection. Then, the use of the elements in the system is described in greater detail.

This paragraph names the labelled parts of the system illustrated in FIG. 1. The system includes four training datasets: pathogenic missense training examples 121, supplemental benign training examples 131, benign missense training examples 161 and supplemental benign training examples 181. The system further includes a trainer 114, a tester 116, a position frequency matrix (PFM) calculator 184, an input encoder 186, a variant pathogenicity prediction model 157, and network(s) 155. The supplemental benign training examples 131 correspond to the pathogenic missense training examples 121 and are therefore placed together in a box with broken lines. Similarly, supplemental benign training examples 181 correspond to the benign missense training examples 161 and therefore, both datasets are shown in the same box.

The system is described with PrimateAI as an example variant pathogenicity prediction model 157 which takes as input amino acid sequences flanking the variant of interest and orthologous sequence alignments in other species. The detailed architecture of the PrimateAI model for pathogenicity prediction is presented above in reference to FIG. 3. The input of the amino acid sequence includes the variant of interest. The term "variant" refers to an amino acid sequence that is different from an amino acid reference sequence. A tri-nucleotide base sequence (also referred to as a codon) at specific positions in protein-coding regions of the chromosome express an amino acid. There are twenty types of amino acids that can be formed by sixty one tri-nucleotide sequence combinations. More than one codon or tri-nucleotide sequence combinations can result in the same amino acid. For example, the codons "AAA" and "AAG" represent Lysine amino acid (also referred to by a symbol "K").

An amino acid sequence variant can be caused by a single nucleotide polymorphism (SNP). SNP is a variation in a single nucleotide that occurs at a specific locus in the gene and is observed to some appreciable degree within a population (e.g., >1%). The technology disclosed focuses on SNPs that occur in protein-coding regions of a gene called exons. There are two types of SNPs: a synonymous SNP and a missense SNP. A synonymous SNP is a type of protein-coding SNP that changes a first codon for an amino acid into a second codon for the same amino acid. A missense SNP on the other hand includes change of a first codon for a first amino acid into a second codon for a second amino acid.

Figure 6:
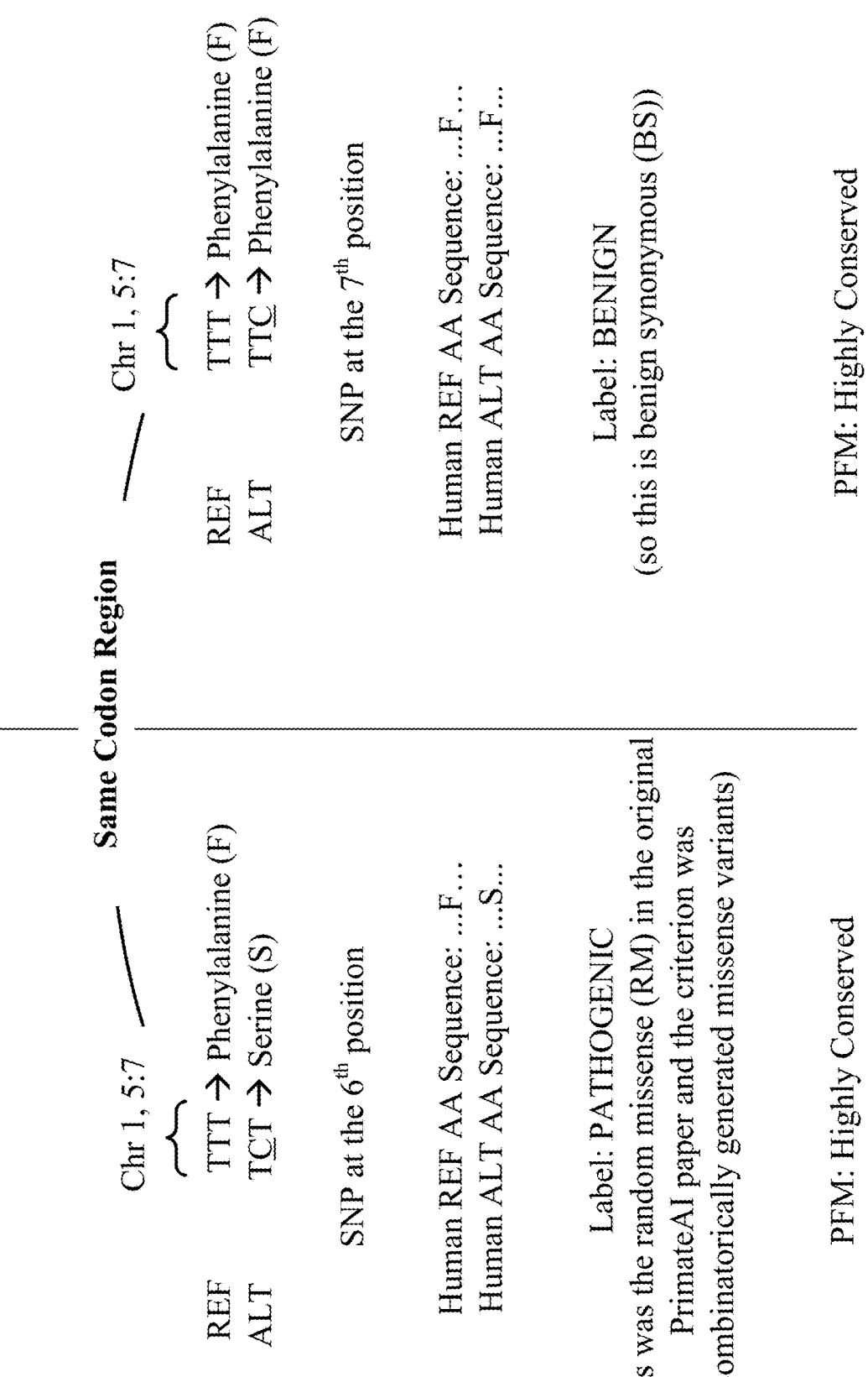
FIG. 6 presents an example missense variant and corresponding supplemental benign training example.

FIG. 6 presents an example 600 of "protein sequence pairs" for a missense variant and a corresponding constructed synonymous variant. The phrase "protein sequence pair" or simply a "sequence pair" refers to a reference protein sequence and an alternative protein sequence. The reference protein sequence comprises reference amino acids expressed by reference codons or tri-nucleotide bases. The alternative protein sequence comprises alternative amino acids expressed by alternative codons or tri-nucleotide bases such that the alternative protein sequence results due to a variant occurring in the reference codon that expresses the reference amino acids of the reference protein sequence.

In FIG. 6 we present construction of a supplemental benign synonymous counterpart training example (referred above as supplemental benign training example) corresponding to a missense variant. The missense variant can be a pathogenic missense training example or a benign missense training example. Consider, the protein sequence pair for a missense variant with a reference amino acid sequence that has a codon "TTT" in chromosome 1 at positions 5, 6, and 7 (i.e., 5:7). Now consider a SNP occurs in the same chromosome at position 6 resulting in an alternate sequence with codon "TCT" at the same positions i.e., 5:7. The codon "TTT" in the reference sequence results in Phenylalanine (F) amino acid whereas the codon "TCT" in the alternative amino acid sequence results in Serine (S) amino acid. To simplify the illustration, FIG. 6 only shows amino acids and corresponding codons in the sequence pairs at target location. Flanking amino acids and respective codons in the sequence pairs are not shown. In the training dataset, the missense variant is labeled as pathogenic (labeled as "1"). To reduce overfitting of the model during training, the technology disclosed constructs a counterpart supplemental benign training example for the corresponding missense variant. The reference sequence in the sequence pair for the constructed supplemental benign training example is the same as the reference sequence in the missense variant shown in the left part of FIG. 6. The right part of FIG. 6 shows a supplemental benign training example which is a synonymous counterpart with the same reference sequence codon "TTT" in chromosome 1 at positions 5:7 as in the reference sequence for missense variant. The alternative sequence constructed for synonymous counterpart has a SNP at position number 7 which results in a codon "TTC". This codon results in the same amino acid Phenylalanine (F) in the alternate sequence as in the reference sequence at the same position in the same chromosome. Two different codons in the same chromosome at the same positions express the same amino acid therefore, the synonymous counterpart is labeled as benign (or labeled as "0"). The two different codons in the same position in the reference and the alternative sequence express the same amino acid at the target location. The benign counterpart is not randomly constructed; instead it is selected from synonymous variants observed in a sequenced population. The technology disclosed constructs supplemental benign training examples to contrast the pathogenic missense training example to reduce overfitting of the variant pathogenicity prediction model during training.

A supplemental benign training example need not be synonymous. The technology disclosed can also construct supplemental benign training examples having the same amino acid in the alternate sequence that are constructed by identical tri-nucleotide codons as in the reference sequence. The associated position frequency matrix (PFM) is the same for identical amino acid sequences, regardless of whether the amino acids are expressed by synonymous or identical codons. Therefore, such supplemental training examples have the same effect of reducing the overfitting of the variant pathogenicity prediction model during training as synonymous counterpart training example presented in FIG. 6.

We now describe the other elements of the system presented in the FIG. 1. The trainer 114 uses the four training datasets presented in FIG. 1 to train the variant pathogenicity prediction model. In one implementation, the variant pathogenicity prediction model is implemented as a convolutional neural network (CNN). The training of CNN is described above with reference to FIG. 5. During training the CNN is adjusted or trained so that the input data leads to a specific output estimate. Training includes adjusting the CNN using back propagation based on a comparison of the output estimate and the ground truth until the output estimate progressively matches or approaches the ground truth. Following training, the tester 116 uses test dataset to benchmark the variant pathogenicity prediction model. The input encoder 186 converts categorical inputs data such as reference and alternative amino acid sequences into a form that can be provided as input to the variant pathogenicity prediction model. This is further explained using example reference and alternative sequences in FIG. 13.

The PFM Calculator 184 calculates the position frequency matrix (PFM) which is also referred to as position-specific scoring matrix (PSSM) or position weight matrix (PWM). The PFM indicates frequency of every amino acid (along vertical axis) at each amino acid position (along horizontal axis) as shown in FIGS. 10 and 11. The technology disclosed calculates three PFMs, one each for primates, mammals and vertebrates. The length of amino acid sequences for each of the three PFMs can be 51 with a target amino acid flanked upstream and downstream by at least 25 amino acids. The PFMs have 20 rows for amino acids and 51 columns for positions of amino acids in the amino acid sequences. The PFM calculator calculates the first PFM with amino acid sequences for 11 primates, the second PFM with amino acid sequences for 48 mammals and a third PFM with amino acid sequences for 40 vertebrates. A cell in a PFM is a count of the occurrences of an amino acid at a specific position in the sequence. The amino acid sequences for the three PFMs are aligned. This means that results of position-wise calculation for primate, mammal and vertebrate PFMs for each amino acid position in the reference amino acid sequence or the alternative amino acid sequence are stored on the position-wise or ordinal position-basis in the same order as the amino acid positions occur in the reference amino acid sequence or the alternative amino acid sequence.

Figure 7:
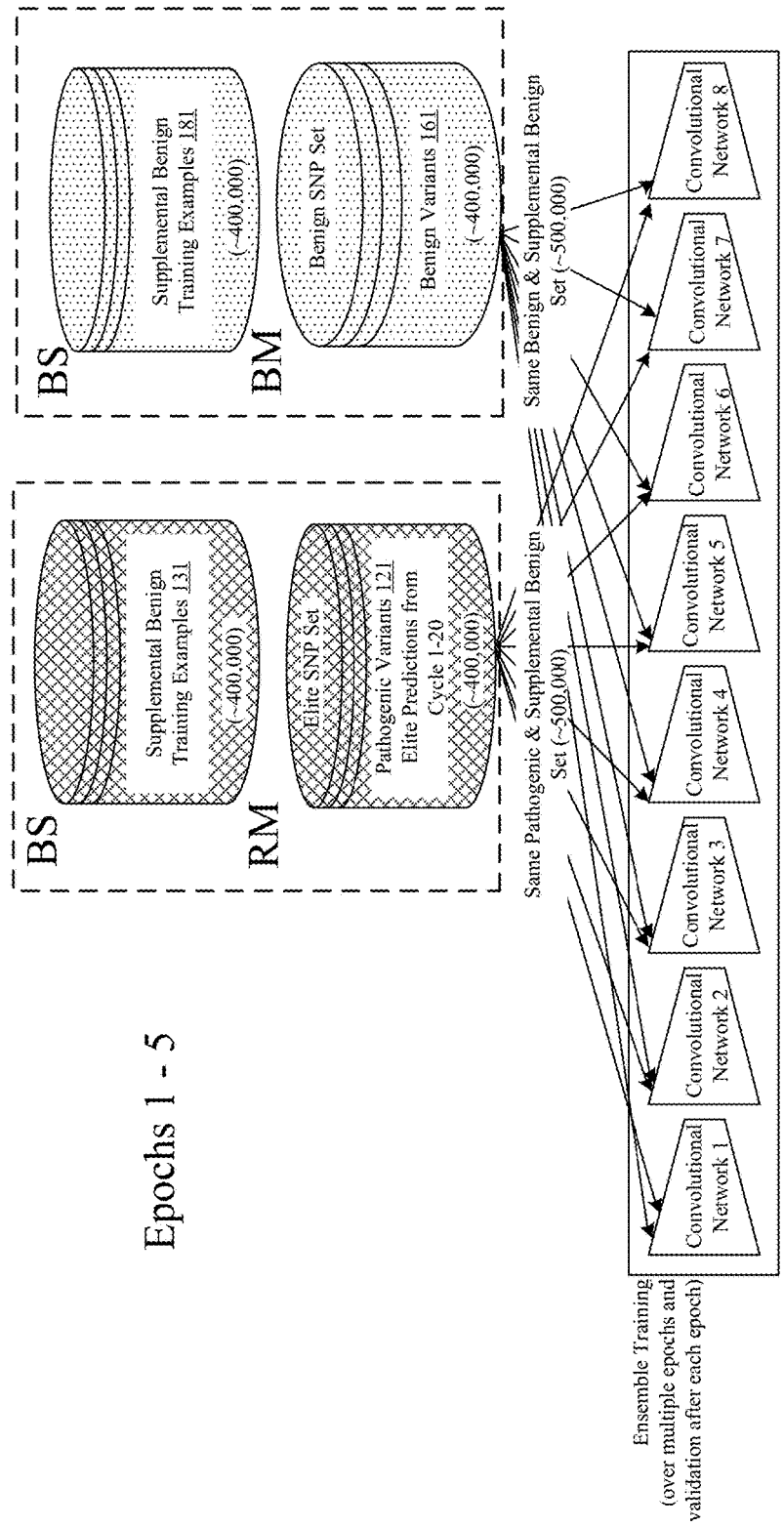
FIG. 7 illustrates disclosed pre-training of the pathogenicity prediction model using supplementary datasets.
Figure 9:
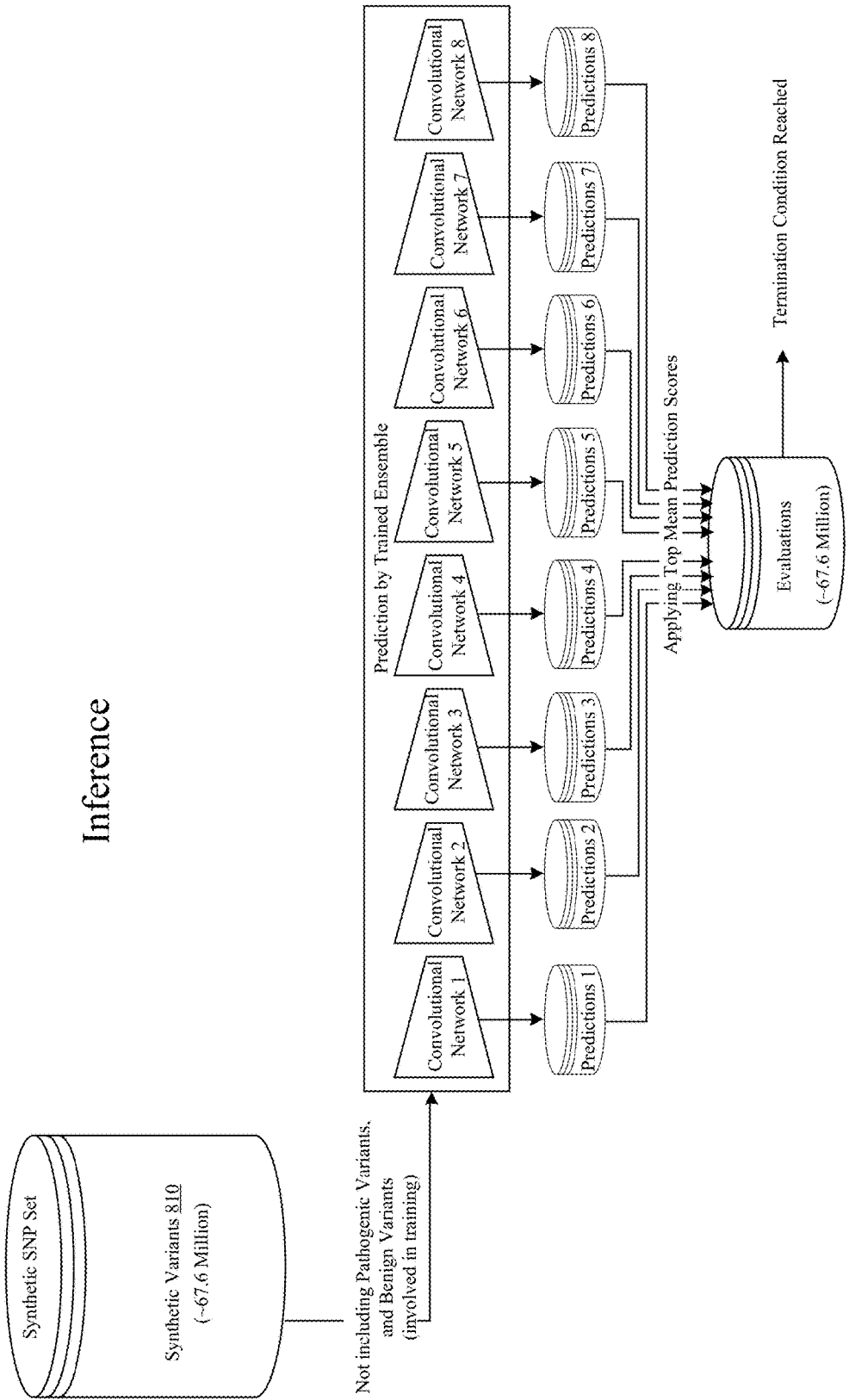
FIG. 9 illustrates application of the trained pathogenicity prediction model to evaluate unlabeled variants.

The technology disclosed uses supplemental benign training examples 131 and 181 during initial training epochs, for example 2 or 3 or 5 or 8 or 10 epochs or 3 to 5, 3 to 8 or 2 to 10 epochs. FIGS. 7, 8, and 9 illustrate the pathogenicity prediction model during pre-training epochs, training epochs and inference. FIG. 7 presents an illustration 700 of pre-training epochs 1 to 5 in which approximately 400,000 benign supplemental training examples 131 are combined with approximately 400,000 pathogenic variants 121 predicted from the deep learning models. Fewer benign supplemental training examples such as approximately 100,000, 200,000 or 300,000 can be combined with pathogenic variants. In one implementation, the pathogenic variant dataset is generated in 20 cycles using random samples from approximately 68 million synthetic variants as described above. In another implementation, the pathogenic variant dataset can be generated in one cycle from approximately 68 million synthetic variants. The pathogenic variants 121 and supplemental benign training examples 131 are given as input to an ensemble of networks in the first five epochs. Similarly, approximately 400,000 supplemental benign training examples 181 are combined with approximately 400,000 benign variants 161 for ensemble training during pre-training epochs. Fewer benign training examples such as approximately 100,000, 200,000 or 300,000 can be combined with benign variants.

The supplemental benign datasets 131 and 181 are not given as input for the rest of the training epochs 6 to n as shown in example 800 in FIG. 8. The training of the ensemble of networks continues over multiple epochs with pathogenic variants dataset and benign variants dataset. The training is terminated after a predetermined number of training epochs or when a termination condition is reached. The trained network is used during inference to evaluate synthetic variants 810 as shown in example 900 in FIG. 9. The trained network predicts a variant as pathogenic or benign.

We now explain a PFM for an example supplemental benign training example 1012 which is constructed as a counterpart of a pathogenic missense variant training example 1002, illustrated in FIG. 10 (referred to by a numeral 1000). A PFM is generated or referenced for a training example. The PFM for the training example depends only on the position of the reference sequence, so both training examples 1002 and 1012 have the same PFM. For example in FIG. 10, two training examples are shown. The first training example 1002 is a pathogenic/unlabeled variant. The second training example 1012 is a counterpart supplemental benign training example corresponding to the training example 1002. The training example 1002 has a reference sequence 1002R and an alternative sequence 1002A. A first PFM is accessed or generated for the training example 1002 based only on the position of reference sequence 1002R. Training example 1012 has a reference sequence 1012R and alternative sequence 1012A. The first PFM for example 1002 can be reused for example 1012. The PFM is calculated using amino acid sequences from multiple species, such as 99 species of primates, mammals, and vertebrates, as an indication of conservation of sequences across species. Humans may or may not be among the species represented in calculation of the PFM. The cells in this PFM include counts of occurrences of amino acids, across species, in the sequences. PFM 1022 is a starting point for a PFM, which illustrates one hot encoding of a single sequence in a training example. When a PFM is complete, for the example of 99 species, positions that are completely conserved across species will have a value of "99" instead of "1". Partial conservation will result in two or more rows in a column having values that sum to 99, in this example. The reference and alternative sequences both have the same PFM, because the PFM depends on the overall sequence position, not on the amino acid in the center position of the sequence.

We now describe the determination of the PFM 1012 using the positions in the example reference sequences in FIG. 10. The example reference and alternative amino acid sequences for both pathogenic/unlabeled training example 1002 and supplemental benign training example 1012 as shown in FIG. 10 have 51 amino acids. The reference amino acid sequence 1002R has Arginine amino acid represented by "R" at position 26 (also referred to as target position) in the sequence. Note that at the nucleotide level, one of the six tri-nucleotide bases or codons (CGT, CGC, CGA, CGG, AGA, and AAG) expresses amino acid "R". We are not showing those codons in this example to simplify the illustration and rather focus on calculation of PFMs. Consider an amino acid sequence (not shown) from one of the 99 species that is aligned to the reference sequence and has an amino acid "R" at position 26. This will result in a value of "1" in the PFM 1022 in the cell at the intersection of row "R" and column "26". Similar values are determined for all columns of the PFM. The two PFMs (i.e., the PFM for the reference sequence 1002R for pathogenic missense variant 1002 and the PFM for the reference sequence 1012R for supplemental benign training example 1012) are the same but for illustration purposes only one PFM 1022 is shown. These two PFMs, represent opposing examples of pathogenicity for the relevant amino acid. One is labeled pathogenic or "1" and the other is labeled "0" for benign. The technology disclosed therefore, reduces overfitting by providing these examples to the model during training.

We construct a second set of supplemental benign training examples 181 that correspond to benign missense variants 161 in the training dataset. FIG. 11 presents an example 1100 in which two PFMs are calculated for an example benign missense variant 1102 and corresponding supplemental benign training example 1122. As seen in the example, reference sequences 1102R and 1112R are the same for both benign missense variant 1102 and supplemental benign training example 1112. Their respective alternative sequences 1102A and 1112A are also shown in the FIG. 11. Two PFMs are generated or referenced for the two reference sequences as describe above for the example presented in FIG. 10. Both PFMs are same, only one PFM 1122 is shown in FIG. 11 for illustration purposes. Both of these PFMs represent benign ("0") labeled amino acid sequences.

Figure 12:
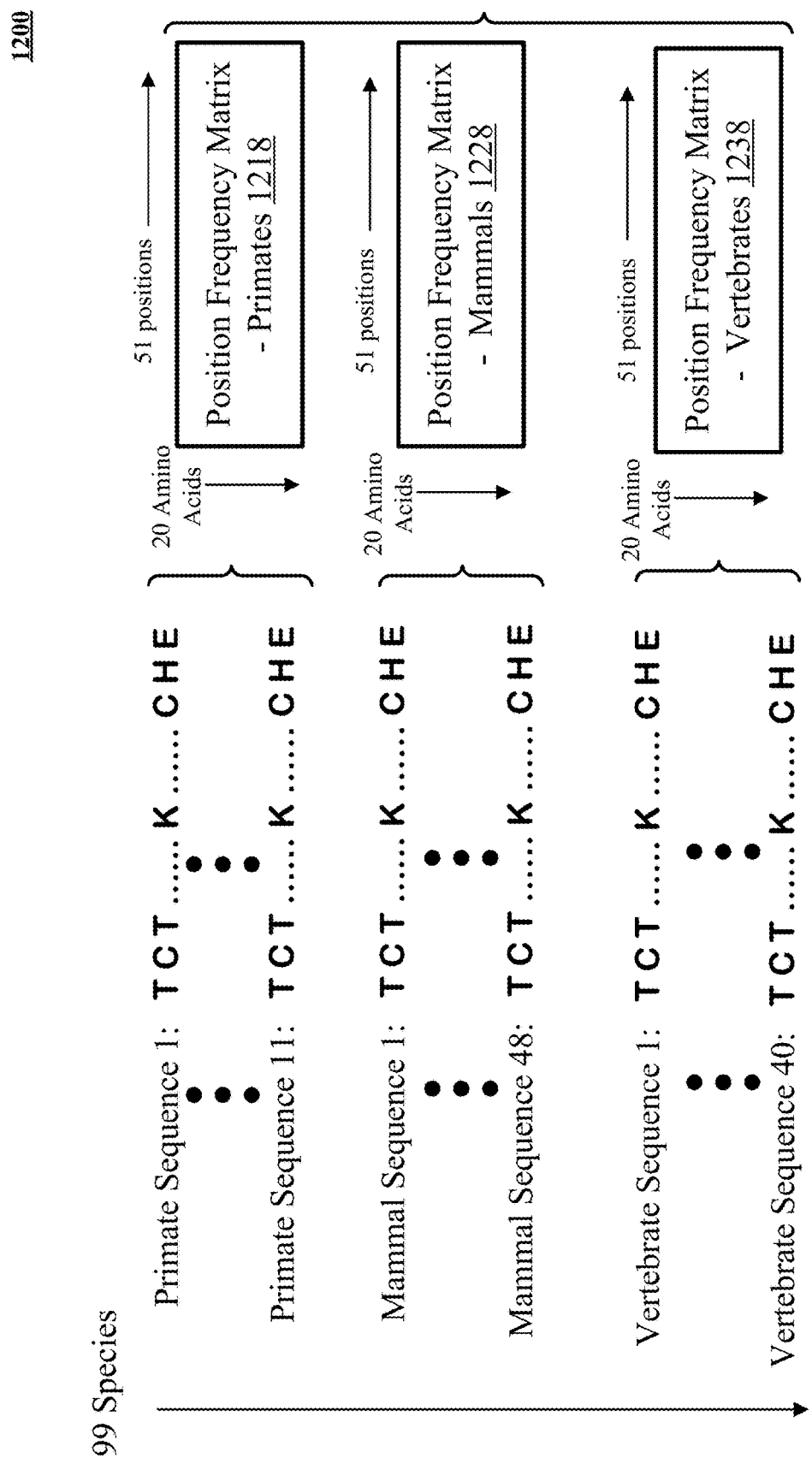
FIG. 12 illustrates construction of position frequency matrices for primate, mammal, and vertebrate amino acid sequences.

The technology disclosed calculates three PFMs one each for 11 primate sequences, 48 mammal sequences and 40 vertebrate sequences. FIG. 12 illustrates the three PFMs 1218, 1228, and 1238 each with 20 rows and 51 columns. In one implementation, the primate sequences do not include human reference sequence. In another implementation, the primate sequences include the human reference sequence. The values of cells in the three PFMs are calculated by counting occurrences of an amino acid (row label) that is present in all sequences for the PFM at a given position (column label). For example, if three primate sequences have an amino acid "K" at position 26, the value of the cell with row label "K" and column label "26" has a value of "3".

Figure 14:
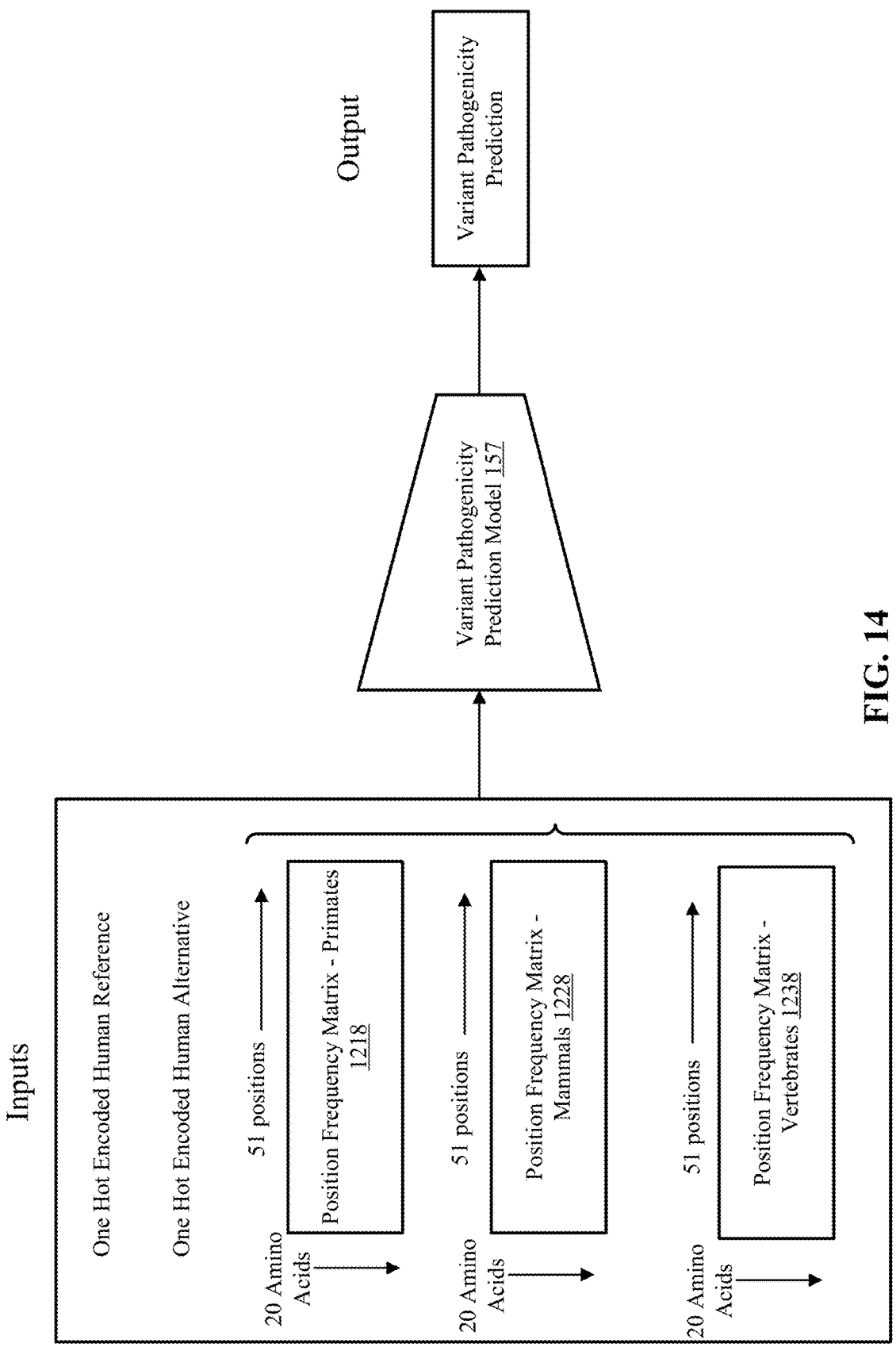
FIG. 14 presents examples of inputs to the variant pathogenicity prediction model.

One hot encoding is a process by which categorical variables are converted into a form that can be provided an input to a deep learning model. A categorical value represents an alpha-numerical value for an entry in the dataset. For example, the reference and alternative amino acid sequences each have 51 amino acid characters arranged in a sequence. An amino acid character "T" at position "1" in a sequence represents an amino acid Threonine at the first position in the sequence. The amino acid sequences are encoded by assigning a value of "1" in the cell with row label "T" and column label "1" in the one hot encoded representation. The one hot encoded representation for an amino acid sequence has 0s in the cells except the cells which represent amino acid (row label) occurring in a particular position (column label). FIG. 13 illustrates an example 1300 in which reference and alternative sequence for a supplemental benign training example are represented as one hot encoded. The reference and alternative amino acid sequences are given as input one hot encoded form to the variant pathogenicity prediction model. FIG. 14 includes an illustration 1400 depicting the inputs to the variant pathogenicity prediction model. The inputs include human reference and alternative amino acid sequences in one hot encoded form and the PFM 1218 for primates, the PFM 1228 for mammals and the PFM 1238 for vertebrates. As described above, the PFM for primates can include only non-human primates or human and non-human primates.

Variations on this approach to supplementing a training set apply both to the architecture described in the applications incorporated by reference and to any other architecture that uses PFMs in combination with other data types, especially in combination with sequences of amino acids or nucleotides.

Results

The performance of the neural network-based model (e.g., the PrimateAI model presented above) improves by using the pre-training epochs presented above. The following table presents example test results. The results in the table are organized under six headings. We briefly describe the headings before presenting the results. "Replicate" columns presents results for 20 replicate runs. Each run can be an ensemble of eight models with different random seeds. "Accuracy" is the proportion of withheld 10,000 primate benign variants that are classified as benign. "Pvalue_DDD" presents results of Wilcoxon rank test to evaluate how well the separation of de novo mutations of affected children with developmental disorders from their unaffected siblings. "pvalue_605genes" presents results of similar tests as pvalue_DDD, except in this case we used de novo mutations within the 605 disease related genes. "Corr_RK_RW" presents the correlation of primateAI scores between amino acid change from R to K and from R to W. A smaller value of Corr_RK_RW indicates better performance. "Pvalue_Corr" presents the pvalue of the correlation in the previous column, i.e., Corr_RK_RW.

The results show that median accuracy of prediction of benign variants using median scores of unknown variants as cutoffs is 91.44% across 20 replicate runs. The log p-value of Wilcoxon rank sum test is 29.39 for separating de novo missense variants of DDD patients from de novo missense variants of controls. Similarly, the log p-value of the rank sum test is 16.18 comparing de novo missense variants within only 605 disease genes. The metrics improved over the previously reported results. The correlation between R→K and R→W is significantly reduced, measured by Wilcoxon rank sum test p-value=3.11e-70.

| Replicate | Accuracy | pvalue_DDD | pvalue_605genes | Corr_RK_RW | pvalue_Corr |
|---|---|---|---|---|---|
| 1 | 0.9184 | 30.1704164 | 15.7534316 | −17.184881 | 3.45E−66 |
| 2 | 0.9161 | 29.474828 | 16.4989964 | −17.359532 | 1.67E−67 |
| 3 | 0.9132 | 28.8581065 | 16.2404644 | −17.43338 | 4.60E−68 |
| 4 | 0.9173 | 30.620667 | 16.5680206 | −20.186589 | 1.28E−90 |
| 5 | 0.9144 | 30.4168273 | 16.6494145 | −17.010813 | 6.83E−65 |
| 6 | 0.9137 | 28.0455968 | 15.7059372 | −18.391879 | 1.53E−75 |
| 7 | 0.9144 | 29.3222477 | 16.907141 | −16.122347 | 1.78E−58 |
| 8 | 0.9162 | 29.1133776 | 16.1400435 | −15.799615 | 3.13E−56 |
| 9 | 0.9163 | 29.0396701 | 16.2525364 | −18.592037 | 3.73E−77 |
| 10 | 0.9141 | 30.0314688 | 15.8089346 | −17.677724 | 6.23E−70 |
| 11 | 0.917 | 31.1082452 | 16.3735087 | −20.615664 | 1.99E−94 |
| 12 | 0.9139 | 29.9753127 | 15.8089346 | −19.394116 | 8.65E−84 |
| 13 | 0.9125 | 29.125927 | 15.7930664 | −12.664288 | 9.33E−37 |
| 14 | 0.9171 | 30.0668966 | 15.2623027 | −19.136444 | 1.26E−81 |
| 15 | 0.9162 | 29.3983163 | 16.1601022 | −18.591003 | 3.80E−77 |
| 16 | 0.9158 | 29.6349726 | 16.1962399 | −19.192294 | 4.29E−82 |
| 17 | 0.9144 | 28.8737094 | 16.3250646 | −20.130602 | 3.98E−90 |
| 18 | 0.9137 | 29.3840529 | 16.6657178 | −17.582348 | 3.36E−69 |
| 19 | 0.9133 | 28.6022916 | 15.5560231 | −20.807509 | 3.70E−96 |

-continued

| Replicate | Accuracy | pvalue_DDD | pvalue_605genes | Corr_RK_RW | pvalue_Corr |
|---|---|---|---|---|---|
| 20 | 0.9137 | 28.8301903 | 15.0293929 | −12.385641 | 3.13E−35 |
| Median | 0.9144 | 29.3911846 | 16.178171 | −18.034802 | 3.11E−70 |

Particular Implementations

We describe systems, methods, and articles of manufacture for pre-training a neural network-implemented model that processes sequences of amino acids and accompanying position frequency matrices (PFMs). One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to the memory. The memory is loaded with computer instructions to reduce overfitting of a neural network-implemented model that processes sequences of amino acids and accompanying position frequency matrices (PFMs). The system includes logic to generate benign labeled supplemental training example sequence pairs that include a start location, through a target amino acid location, to an end location. A supplemental sequence pair matches the start location and the end location of a missense training example sequence pair. It has identical amino acids in a reference and an alternate sequence of amino acids. The system includes logic to input with each supplemental sequence pair a supplemental training PFM that is identical to the PFM of the missense training example sequence pair at the matching start and end location. The system includes logic to train the neural network-implemented model using the benign training example sequence pairs and the supplemental training example PFMs, and the missense training example sequence pairs and PFMs of the missense training example sequence pairs at the matching start and end locations. The training influence of the training PFMs is attenuated during the training.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system can include logic to construct supplemental sequence pairs such that each supplemental sequence pair matches the start location and the end location of a benign missense training example sequence pair.

The system can include logic to construct supplemental sequence pairs such that each supplemental sequence pair matches the start location and the end location of a pathogenic missense training example sequence pair.

The system includes logic to modify the training of the neural network-implemented model to cease using the supplemental training example sequence pairs and the supplemental training PFMs after a predetermined number of training epochs.

The system includes logic to modify the training of the neural network-implemented model to cease using the supplemental training example sequence pairs and the supplemental training PFMs after three training epochs.

The system includes logic to modify the training of the neural network-implemented model to cease using the supplemental training example sequence pairs and the supplemental training PFMs after five training epochs.

The ratio of the supplemental training example sequence pairs to the pathogenic training example sequence pairs can be between 1:1 and 1:8. The system can use different values for the ranges for example, between 1:1 and 1:12, between 1:1 and 1:16 and between 1:1 and 1:24.

The ratio of the supplemental training example sequence pairs to the benign training example sequence pairs can be between 1:2 and 1:8. The system can use different values for the ranges for example, between 1:1 and 1:12, between 1:1 and 1:16 and between 1:1 and 1:24.

The system includes logic to create the supplemental PFMs, amino acid locations from data for non-human primates and non-primate mammals.

Other implementations may include a non-transitory computer readable storage medium storing instructions executable by a processor to perform functions of the system described above. Yet another implementation may include a method performing the functions of the system described above.

A method implementation of the technology disclosed includes generating benign labeled supplemental training example sequence pairs that include a start location, through a target amino acid location, to an end location. Each supplemental sequence pair matches the start location and the end location of a missense training example sequence pair. It has identical amino acids in a reference and an alternate sequence of amino acids. The method includes inputting a supplemental training PFM with each supplemental sequence pair that is identical to the PFM of the missense training example sequence pair at the matching start and end location. The method includes training the neural network-implemented model using the benign training example sequence pairs and the supplemental training example PFMs, and the missense training example sequence pairs, and the PFMs of the missense at the matching start and end locations. The training influence of the training PFMs is attenuated during the training.

This method implementation and other methods disclosed optionally include one or more of the following features. Methods can also include features described in connection with systems disclosed. The reader will understand how features identified in this section can readily be combined with base features in other statutory classes.

Other implementations may include a set of one or more non-transitory computer readable storage media collectively storing computer program instructions executable by one or more processors to reduce overfitting of a neural network-implemented model that processes sequences of amino acids and accompanying position frequency matrices (PFMs). The computer program instructions when executed on or more processors implement the method including, generating benign labeled supplemental training example sequence pairs that include a start location, through a target amino acid location, to an end location. Each supplemental sequence pair matches the start location and the end location of a missense training example sequence pair. It has identical amino acids in a reference and an alternate sequence of amino acids The method includes inputting a supplemental training PFM with each supplemental sequence pair that is identical to the PFM of the missense training example sequence pair at the matching start and end location. The method includes training the neural network-implemented model using the benign training example sequence pairs and the supplemental training example PFMs, and the missense training example sequence pairs, and the PFMs of the missense training at the matching start and end locations s. The training influence of the training PFMs is attenuated during the training.

Computer readable media (CRM) implementations of the technology disclosed include one or more a non-transitory computer readable storage media impressed with computer program instructions, when executed on one or more processors, implement the method described above. This CRM implementation includes one or more of the following features. CRM implementation can also include features described in connection with system and method disclosed above.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

Computer System

Figure 15:
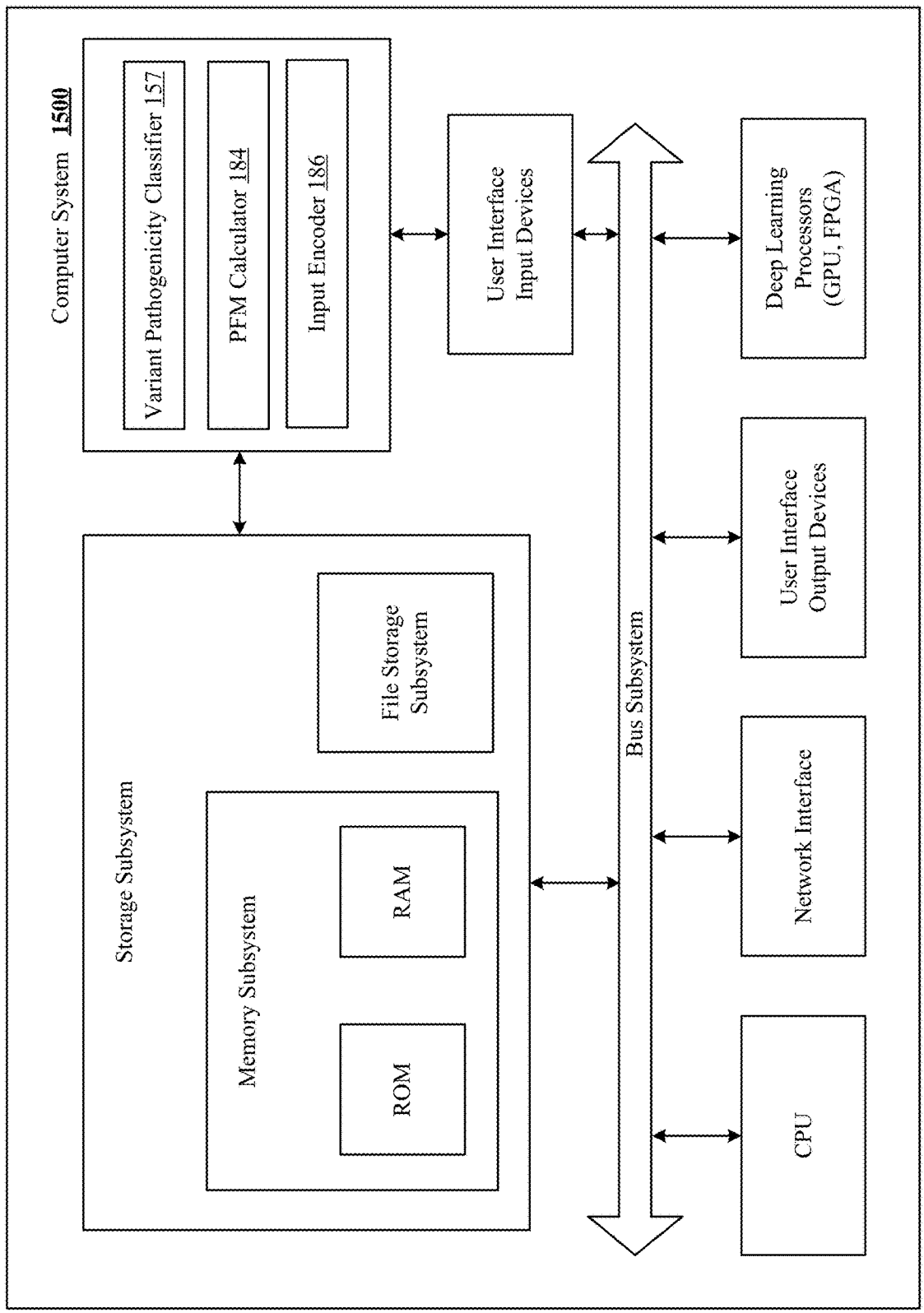
FIG. 15 is a simplified block diagram of a computer system that can be used to implement the technology disclosed.

FIG. 15 is a simplified block diagram 1500 of a computer system that can be used to implement the technology disclosed. Computer system typically includes at least one processor that communicates with a number of peripheral devices via bus subsystem. These peripheral devices can include a storage subsystem including, for example, memory devices and a file storage subsystem, user interface input devices, user interface output devices, and a network interface subsystem. The input and output devices allow user interaction with computer system. Network interface subsystem provides an interface to outside networks, including an interface to corresponding interface devices in other computer systems.

In one implementation, the neural network such as variant pathogenicity classifier 157, the PFM calculator 184 and the input encoder 186 are communicably linked to the storage subsystem and user interface input devices. The User interface input devices can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem stores programming and data constructs that provide the functionality of some or all of the modules and methods described herein. These software modules are generally executed by processor alone or in combination with other processors.

Memory used in the storage subsystem can include a number of memories including a main random access memory (RAM) for storage of instructions and data during program execution and a read only memory (ROM) in which fixed instructions are stored. A file storage subsystem can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 15 is intended only as a specific example for purposes of illustrating the technology disclosed. Many other configurations of computer system are possible having more or less components than the computer system depicted in FIG. 15.

The deep learning processors can be GPUs or FPGAs and can be hosted by deep learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

What is claimed is:

1. A method to reduce overfitting of a neural network-implemented model that processes sequences of amino acids and accompanying position frequency matrices (PFMs), the method including:
   generating supplemental training example sequence pairs, labelled benign, that include a start location, through a target amino acid location, to an end location, wherein each supplemental training example sequence pair:

matches the start location and the end location of a missense training example sequence pair; and has identical amino acids in a reference and an alternate sequence of amino acids;

inputting with each supplemental training example sequence pair a supplemental training PFM that is identical to the PFM of the missense training example sequence pair at the matching start and end location; and training the neural network-implemented model using the benign supplemental training example sequence pairs, the supplemental training PFMs, the missense training example sequence pairs, and the PFMs of the missense training example sequence pairs at the matching start and end locations;

whereby training influence of the supplemental training PFMs is attenuated during the training.

2. The method of claim 1, wherein the supplemental training example sequence pairs match the start location and the end location of pathogenic missense training example sequence pairs.

3. The method of claim 1, wherein the supplemental training example sequence pairs match the start location and the end location of benign missense training example sequence pairs.

4. The method of claim 1, further including: modifying the training of the neural network-implemented model to cease using the supplemental training example sequence pairs and the supplemental training PFMs after a predetermined number of training epochs.

5. The method of claim 1, further including: modifying the training of the neural network-implemented model to cease using the supplemental training example sequence pairs and the supplemental training PFMs after five training epochs.

6. The method of claim 2, further including: a ratio of the supplemental training example sequence pairs to the pathogenic missense training example sequence pairs is between 1:1 and 1:8.

7. The method of claim 3, further including: a ratio of the supplemental training example sequence pairs to the benign missense training example sequence pairs is between 1:1 and 1:8.

8. The method of claim 1, further including: using, in creating the supplemental training PFMs, amino acid locations from data for non-human primates and non-primate mammals.

9. A system including one or more processors coupled to memory, the memory loaded with computer instructions to reduce overfitting of a neural network-implemented model that processes sequences of amino acids and accompanying position frequency matrices (PFMs), the instructions, when executed on the processors, implement actions comprising:

generating supplemental training example sequence pairs, labelled benign, that include a start location, through a target amino acid location, to an end location, wherein each supplemental training example sequence pair:

matches the start location and the end location of a missense training example sequence pair; and has identical amino acids in a reference and an alternate sequence of amino acids;

inputting with each supplemental training example sequence pair a supplemental training PFM that is identical to the PFM of the missense training example sequence pair at the matching start and end location; and training the neural network-implemented model using the benign supplemental training example sequence pairs, the supplemental training PFMs, the missense training example sequence pairs, and the PFMs of the missense training example sequence pairs at the matching start and end locations;

whereby training influence of the supplemental training PFMs is attenuated or counteracted during the training.

10. The system of claim 9, wherein the supplemental training example sequence pairs match the start location and the end location of pathogenic missense training example sequence pairs.

11. The system of claim 9, wherein the supplemental training example sequence pairs match the start location and the end location of benign missense training example sequence pairs.

12. The system of claim 9, further implementing actions comprising: modifying the training of the neural network-implemented model to cease using the supplemental training example sequence pairs and the supplemental training PFMs after a predetermined number of training epochs.

13. The system of claim 9, further implementing actions comprising: modifying the training of the neural network-implemented model to cease using the supplemental training example sequence pairs and the supplemental training PFMs after five training epochs.

14. The system of claim 10, further implementing actions comprising: a ratio of the supplemental training example sequence pairs to the pathogenic missense training example sequence pairs is between 1:1 and 1:8.

15. The system of claim 11, further implementing actions comprising: a ratio of the supplemental training example sequence pairs to the benign missense training example sequence pairs is between 1:1 and 1:8.

16. The system of claim 9, further implementing actions comprising: using, in creating the supplemental training PFMs, amino acid locations from data for non-human primates and non-primate mammals.

17. A non-transitory computer readable storage medium impressed with computer program instructions to reduce overfitting of a neural network-implemented model that processes sequences of amino acids and accompanying position frequency matrices (PFMs), the instructions, when executed on a processor, implement a method comprising:

generating supplemental training example sequence pairs, labelled benign, that include a start location, through a target amino acid location, to an end location, wherein each supplemental training example sequence pair:

matches the start location and the end location of a missense training example sequence pair; and has identical amino acids in a reference and an alternate sequence of amino acids;

inputting with each supplemental training example sequence pair a supplemental training PFM that is identical to the PFM of the missense training example sequence pair at the matching start and end location; and training the neural network-implemented model using the benign supplemental training example sequence pairs, the supplemental training PFMs, missense training example sequence pairs, and the PFMs of the missense training example sequence pairs at the matching start and end locations;

whereby training influence of the supplemental training PFMs is attenuated during the training.

18. The non-transitory computer readable storage medium of claim 17, wherein the supplemental training example sequence pairs match the start location and the end location of pathogenic missense training example sequence pairs.

19. The non-transitory computer readable storage medium of claim 17, wherein the supplemental training example sequence pairs match the start location and the end location of benign missense training example sequence pairs.

20. The non-transitory computer readable storage medium of claim 17, implementing the method further comprising: modifying the training of the neural network-implemented model to cease using the supplemental training example sequence pairs and the supplemental training PFMs after a predetermined number of training epochs.

21. The non-transitory computer readable storage medium of claim 17, implementing the method further comprising: modifying the training of the neural network-implemented model to cease using the supplemental training example sequence pairs and the supplemental training PFMs after five training epochs.

22. The non-transitory computer readable storage medium of claim 18, implementing the method further comprising: a ratio of the supplemental training example sequence pairs to the pathogenic missense training example sequence pairs is between 1:1 and 1:8.

23. The non-transitory computer readable storage medium of claim 19, implementing the method further comprising: a ratio of the supplemental training example sequence pairs to the benign missense training example sequence pairs is between 1:1 and 1:8.

24. The non-transitory computer readable storage medium of claim 17, implementing the method further comprising: using, in creating the supplemental training PFMs, amino acid locations from data for non-human primates and non-primate mammals.

* * * * *